(12) United States Patent
Patil et al.

(10) Patent No.: US 9,056,835 B2
(45) Date of Patent: Jun. 16, 2015

(54) LPA₂ RECEPTOR-SPECIFIC BENZOIC ACID DERIVATIVES

(71) Applicant: University of Tennessee Research Foundation, Memphis, TN (US)

(72) Inventors: Renukadevi Patil, Germantown, TN (US); James Fells, Memphis, TN (US); Duane D. Miller, Germantown, TN (US); Gabor Tigyi, Memphis, TN (US)

(73) Assignee: The University of Tennessee Research Foundation, Memphis, TN (US)

( * ) Notice: Subject to any disclaimer, the term of this patent is extended or adjusted under 35 U.S.C. 154(b) by 0 days.

(21) Appl. No.: 14/011,739

(22) Filed: Aug. 27, 2013

(65) Prior Publication Data
US 2014/0057936 A1    Feb. 27, 2014

Related U.S. Application Data

(60) Provisional application No. 61/693,731, filed on Aug. 27, 2012.

(51) Int. Cl.
*C07D 221/14* (2006.01)
*C07D 417/06* (2006.01)

(52) U.S. Cl.
CPC ............ *C07D 221/14* (2013.01); *C07D 417/06* (2013.01)

(58) Field of Classification Search
CPC ..................................................... C07D 221/14
USPC ........................ 546/99, 143; 514/296; 544/63
See application file for complete search history.

(56) References Cited

U.S. PATENT DOCUMENTS

| | | | |
|---|---|---|---|
| 4,204,063 A | 5/1980 | Brana et al. | |
| 6,486,173 B2 * | 11/2002 | Cain et al. | 514/307 |
| 2005/0239833 A1 | 10/2005 | Kazantsev et al. | |
| 2005/0288340 A1 | 12/2005 | Hamanaka | |
| 2010/0189685 A1 | 7/2010 | Byrd | |

FOREIGN PATENT DOCUMENTS

WO         9504048         2/1995

OTHER PUBLICATIONS

ISR of the corresponding PCT/US2013/056911, Feb. 10, 2014.

* cited by examiner

*Primary Examiner* — Rita Desai
(74) *Attorney, Agent, or Firm* — Lihua Zheng; Proskauer Rose LLP

(57) ABSTRACT

Disclosed are compounds effective for inhibiting cellular apoptosis and for protecting cells and tissues from the apoptotic effects of chemotherapeutic agents and/or ionizing radiation. Compounds of the invention act as agonists of the LPA₂ receptor. Compounds of the invention comprise non-lipid benzoic acid derivatives.

2 Claims, 21 Drawing Sheets

A

B

C

D

Figure 1 Chemical structures of LPA 18:1, Octadecenyl thiophosphate (OTP) and GRI977143

Figure.2 Structural modifications of compound 5b

Scheme-1

Scheme-2

Scheme-3

LPA$_2$ RECEPTOR-SPECIFIC BENZOIC ACID DERIVATIVES

CROSS-REFERENCE TO RELATED APPLICATIONS

This application claims the benefit of priority of U.S. Provisional Patent Application No. 61/693,731, filed Aug. 27, 2012, the contents of which are incorporated herein by reference.

FIELD OF THE INVENTION

The invention relates to compositions comprising new benzoic acid derivatives. More specifically, the invention relates to compounds comprising new sulfamoyl benzoic acid derivatives, these compounds acting as LPA$_2$ receptor agonists.

BACKGROUND OF THE INVENTION

The growth factor-like lysophospholipids lysophosphatidic acid (LPA) and sphingosine-1-phosphate (S1P) regulate many fundamental cellular responses, including cell survival, cell proliferation, cellular motility and migration. LPA has been shown to have profound activity in preventing apoptosis and rescuing cells from the progression of the apoptotic cascade. An LPA mimic, octadecenyl thiophosphate (OTP) (Durgam et al., Synthesis and pharmacological evaluation of second-generation phosphatidic acid derivatives as lysophosphatidic acid receptor ligands. *Bioorg Med Chem Lett* (2006) 16(3): 633-640), has demonstrated superior efficacy in vitro and in vivo, as compared to LPA, in rescuing cells and animals from radiation-induced apoptosis (Deng et al., The lysophosphatidic acid type 2 receptor is required for protection against radiation-induced intestinal injury. *Gastroenterology* (2007) 132(5): 1834-1851).

The G protein-coupled lysophosphatidic acid 2 (LPA$_2$) receptor elicits prosurvival responses to prevent and rescue cells from apoptosis. LPA$_2$ stimulation provides protection from chemotherapeutic agent-induced apoptosis and radiation-induced apoptosis. Highly effective LPA$_2$-specific agonists may therefore have significant therapeutic value.

Development of LPA-based drug candidates has thus far been limited to the discovery of lipid-like ligands, primarily to address the hydrophobic environment of the S1P and LPA G protein-coupled receptor (GPCR) ligand binding pockets. Only a few LPA receptor ligands utilize nonlipid structural features, including Ki16425, an LPA$_{1/2/3}$ antagonist (Ohta et al., Ki16425, a subtype-selective antagonist for EDG-family lysophosphatidic acid receptors. *Mol Pharmacol* (2003) 64(4): 994-1005), and the AM095-152 series of LPA$_1$-selective compounds (Swaney et al., Pharmacokinetic and pharmacodynamic characterization of an oral lysophosphatidic acid type 1 receptor-selective antagonist. *J Pharmacol Exp Ther* (2011) 336(3): 693-700). A major obstacle in developing LPA analogs is their high degree of hydrophobicity that makes these agents non-ideal drug candidates. Another complicating factor is the multiplicity of LPA GPCRs, which represents a significant challenge to the development of compounds specific to a single target such as LPA$_2$.

There are pharmacological advantages to the use of non-lipid molecules as pharmaceutical agents. Discovery and development of drug-like non-lipid compounds might produce even more efficacious molecules that can interact with LPA receptors in ways that will produce desirable cellular and systemic effects.

SUMMARY OF THE INVENTION

The present invention relates to compounds of Formula I

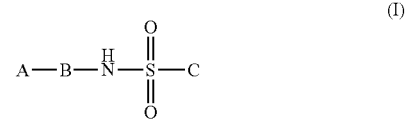

(I)

wherein A is

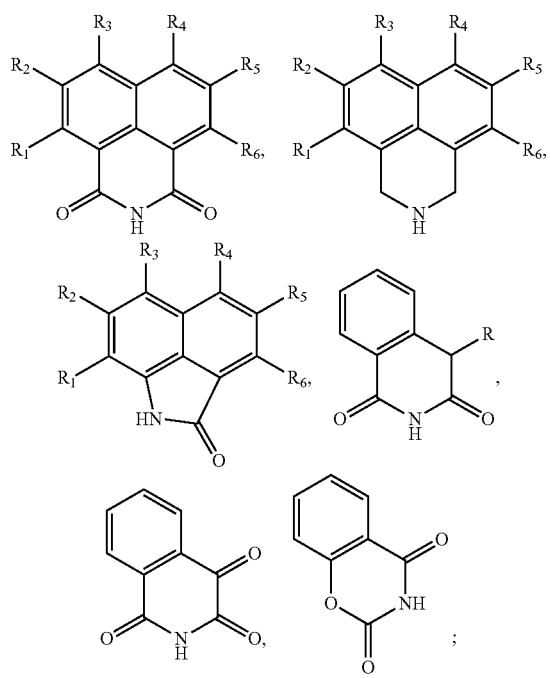

R is H or substituted or unsubstituted phenyl;

R$_1$, R$_2$, R$_3$, R$_4$, R$_5$, and R$_6$ are independently H, NO$_2$, Br, Cl, or OCH$_3$;

B is C$_2$ to C$_8$ alkyl or alkenyl; and

C is

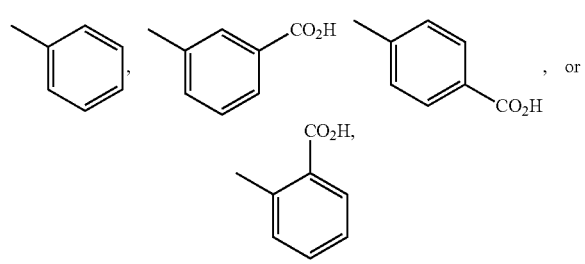

optionally substituted with F, Cl, Br, NO$_2$, NH$_2$, OCH$_3$, CH$_3$, CO$_2$H, or phenyl.

The invention also relates to a method comprising administering to a human and/or animal subject a therapeutically effective amount of one or more compounds of Formula I

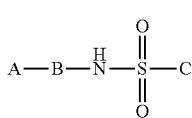

wherein A is

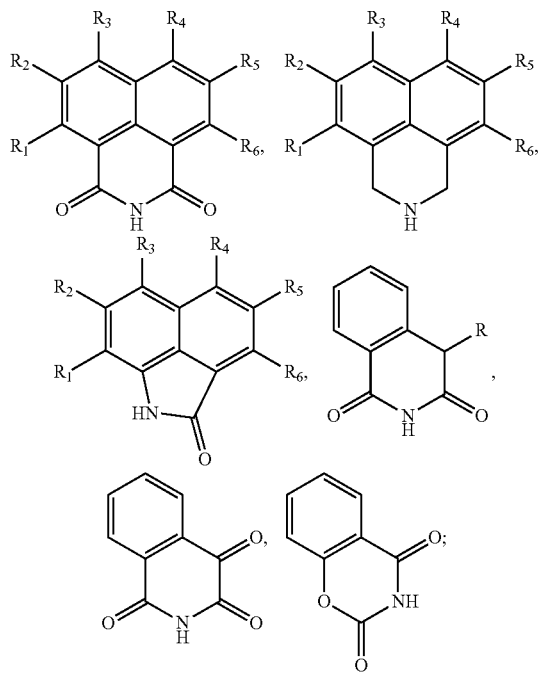

R is H or substituted or unsubstituted phenyl;
$R_1$, $R_2$, $R_3$, $R_4$, $R_5$, and $R_6$ are independently H, $NO_2$, Br, Cl, or $OCH_3$;
B is $C_2$ to $C_8$ alkyl or alkenyl; and
C is

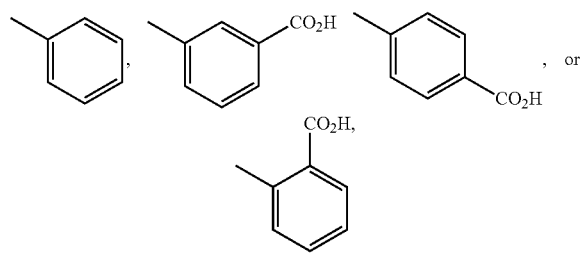

optionally substituted with F, Cl, Br, $NO_2$, $NH_2$, $OCH_3$, $CH_3$, $CO_2H$, or phenyl, to decrease apoptosis in cells and tissues of the subject.

In various aspects of the invention, the method comprises a method of administering a therapeutically-effective amount of a compound of Formula I for decreasing apoptosis in cells and tissues of a human and/or animal subject subjected to chemotherapeutic agents and/or radiation. In various aspects, the radiation may be ionizing radiation.

DETAILED DESCRIPTION

Figure 1:
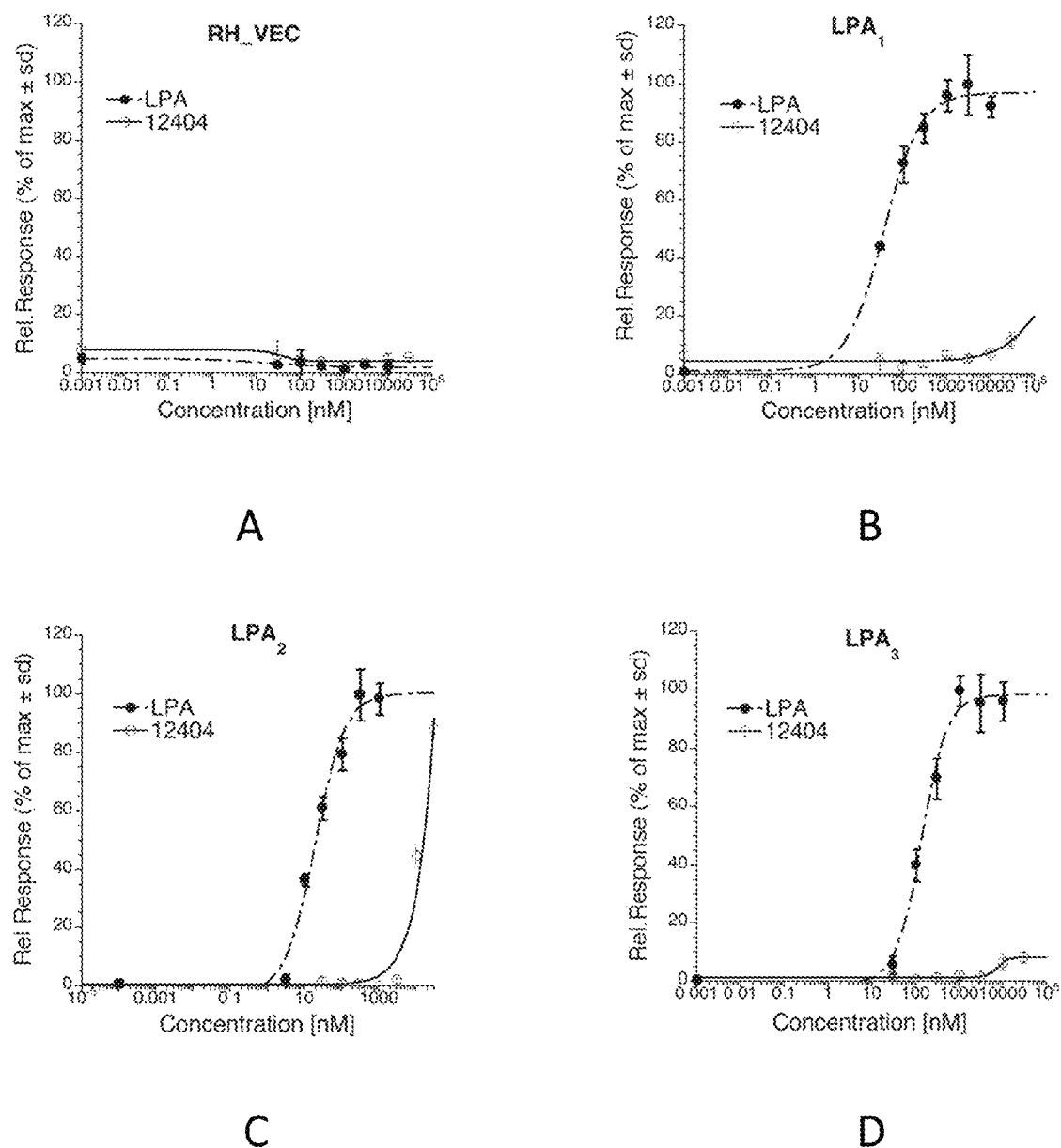
FIG. 1 is a series of 4 graphs illustrating receptor specificity of the prototype hit compound NSC12404 indicated by LPA GPCR-activated $Ca^{2+}$-transients in cell lines expressing the individual LPA GPCR subtypes. The curves shown in this figure are representative of at least two experiments.
Figure 2:
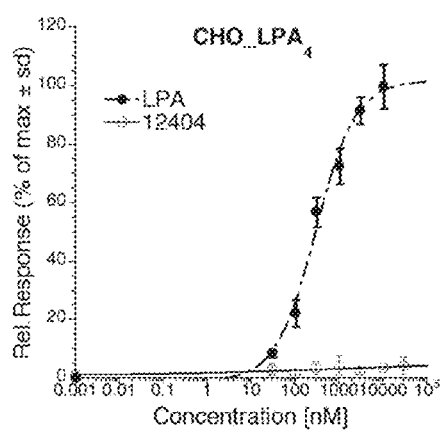
FIG. 2 is a series of 4 graphs illustrating receptor specificity of the prototype hit compound NSC12404 indicated by LPA GPCR-activated $Ca^{2+}$-transients in cell lines expressing the individual LPA GPCR subtypes. The curves shown in this figure are representative of at least two experiments.
Figure 2:
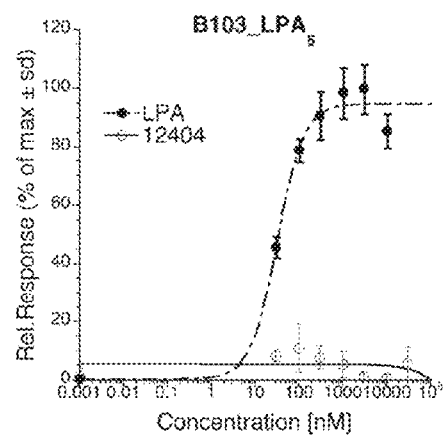
Figure 2:
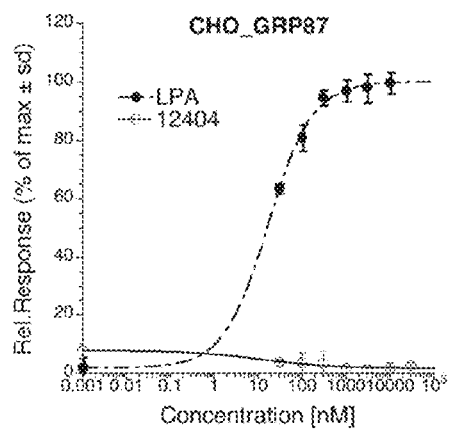
Figure 2:
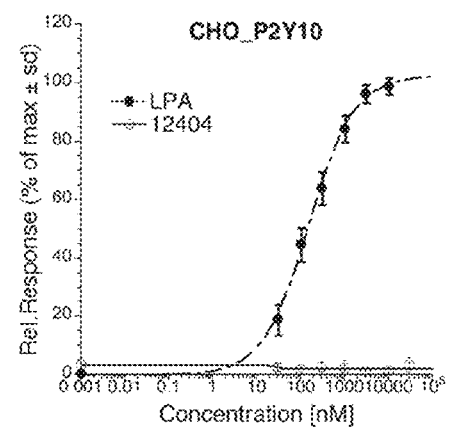

The inventors have developed compounds comprising benzoic acid derivatives that are useful as LPA$_2$ receptor-specific agonists, these compounds being effective for inhibiting apoptosis in damaged cells such as, for example, cells damaged by irradiation and/or by exposure to chemotherapeutic agents such as those used for cancer chemotherapy. The compounds are also effective for promoting cell growth, and may be used either therapeutically or, for example, in tissue culture, to promote growth of target cells. LPA has been associated with increased cell survival in macrophages, Schwann cells, T lymphocytes, fibroblasts, endothelial cells, and osteoblastic cells. Current evidence suggests that this is an LPA$_2$-mediated effect. Therefore, compositions comprising compounds of the invention may also have therapeutic effect in a variety of conditions such as immune disorders, bone remodeling after injury, endothelial dysfunction, and congestive heart failure.

Compounds of the invention comprise compounds of Formula I

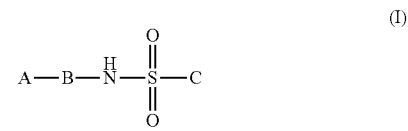

wherein A is

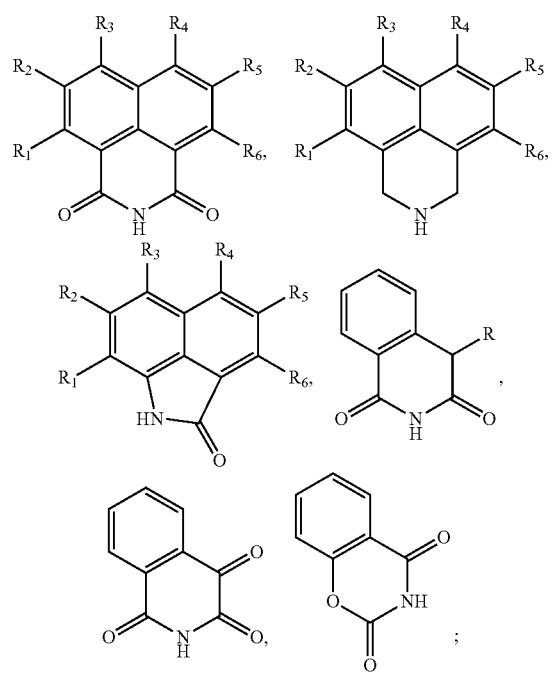

R is H or substituted or unsubstituted phenyl;

$R_1$, $R_2$, $R_3$, $R_4$, $R_5$, and $R_6$ are independently H, $NO_2$, Br, Cl, or $OCH_3$;

B is $C_2$ to $C_8$ alkyl or alkenyl; and

C is

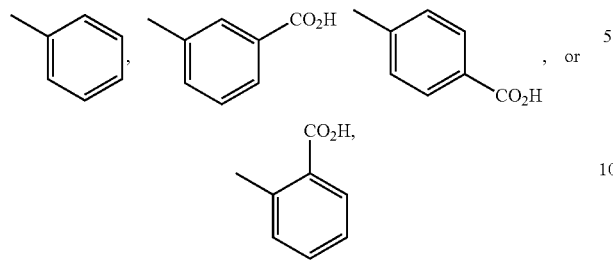

optionally substituted with F, Cl, Br, $NO_2$, $NH_2$, $OCH_3$, $CH_3$, $CO_2H$, or phenyl.

The inventors applied virtual screening strategies using similarity searching that they had previously derived from validated molecular models of these receptors. They limited their searches to chemical libraries with drug-like compounds that satisfy Lipinski's rule of five (Lipinski, 2003). They focused their virtual screen on the discovery of ligands for the $LPA_2$ receptor subtype because of its role in programmed cell death associated with radiation and chemotherapy (Deng et al., 2007).

The inventors used the virtual screening method to identify four non-lipid compounds that are specific agonists of $LPA_2$:

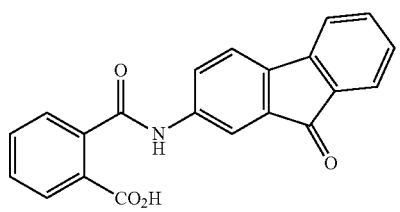

NSC12404
2-((9-oxo-9H-fluoren-2-yl)carbamoyl)benzoic acid

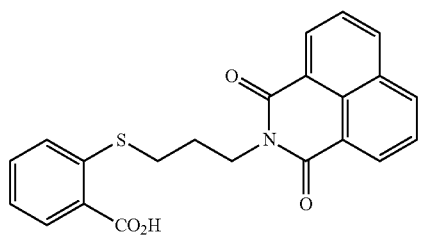

GRI997143
2-((3-(1,3-dioxo-1H-benzo[de]isoquinolin-2(3H)-yl)propyl)thio)benzoic acid

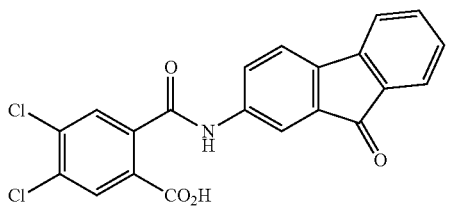

H2L 5547294
4,5-dichloro-2-((9-oxo-9H-fluoren-2-yl)carbamoyl)benzoic acid

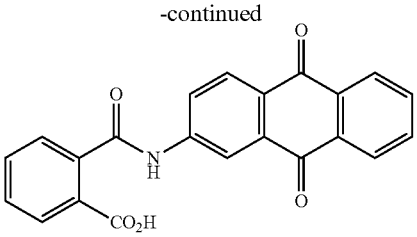

H2L58182102
2-((9,10-dioxo-9,10-dihydroanthracen-2-yl)carbamoyl)benzoic acid

They selected one of these hits (GRI977143 from the Genome Research Institute (GRI) chemical library), and characterized its cellular and signaling responses in several assay systems. Their results demonstrated that the compound GRI977143 is a specific agonist of $LPA_2$ and does not activate any other known or putative LPA GPCR. The inventors have also shown that GRI977143 is effective in a similar manner to LPA in preventing programmed cell death, although in $Ca^{2+}$-mobilization and caspase 3 and 7 inhibition assays it has a higher $EC_{50}$ than LPA. GRI977143 inhibited activation of caspases 3, 7, 8, and 9, B-cell lymphoma 2 (Bcl-2)-associated X protein (Bax) translocation, and poly (ADP-ribose) polymerase 1 (PARP-1) cleavage, leading to reduced DNA fragmentation following activation of the extrinsic or intrinsic apoptotic signaling cascades. They also demonstrated that GRI977143 robustly activates the extracellular signal regulated kinases 1/2 (ERK1/2) survival pathway and leads to the assembly of a macromolecular signalosome consisting of $LPA_2$, thyroid receptor interacting protein 6 (TRIP6), and $Na^+$—$H^+$ exchange regulatory factor 2 (NHERF2), which has been shown to be required for the pro-survival signaling elicited via this receptor subtype, further confirming its $LPA_2$ receptor subtype specificity. The invention therefore provides a method for inhibiting apoptosis and increasing cell survival after chemotherapeutic and/or radiation damage to cells and tissues. The method comprises administering to a human and/or animal subject a therapeutically effective dose of GRI977143 to increase cell survival after the human and/or animal subject has been exposed to chemotherapeutic agents and/or ionizing radiation.

Similarity searches were performed separately using each fingerprint to quantitate similarity. Hits meeting the 80% similarity threshold from each search were ranked based on the Tanimoto coefficient measure of similarity to a target molecule NSC12404, and the top 75 unique hits from each fingerprint search were selected for further analysis. The 225 compounds selected for further analysis were clustered based on Tanimoto coefficients calculated using Molecular ACCess System-key fingerprints (MACCS keys) and evaluated using the diversity subset function implemented in MOE. This selected a diverse subset of 27 compounds for biological evaluation by choosing the middle compounds in each cluster. These 27 compounds were tested in $Ca^{2+}$ mobilization assays at a concentration of 10 μM using stable cell lines individually expressing $LPA_2$ and also in vector-transfected control cells. Hits activating $LPA_2$ were further tested using cells expressing the other established and putative LPA GPCRs. Experimental testing of the selected compounds identified the three new selective $LPA_2$ agonists: GRI977143, H2L5547924, and H2L5828102. H2L5547924, H2L5828102 and GRI977143 activated only $LPA_2$ and failed to activate any of the other established and putative LPA GPCRs when applied at levels up to 10 μM. These compounds have also been tested at 10 μM for the inhibition of the $Ca^{2+}$ response elicited by ~$EC_{75}$ concentration of LPA 18:1 at those receptors that the compound failed to activate when applied at 10 μM. The inventors found that at this high concentration NSC12404 and GRI977143 inhibited LPA₃ but none of the other receptors they tested were either activated or inhibited by these two compounds. H2L5547924 not only activated LPA₂ but partially inhibited LPA₁, LPA₄, GPR87, and P2Y10. H2L5828102 not only was a specific agonist of LPA₂ but also fully inhibited LPA₃ and partially inhibited LPA₁, GPR87 and P2Y10. Results are shown in Table 1. They arbitrarily selected GRI977143 for further characterization in cell-based assays.

Chemical shift values were reported as parts per million (δ), coupling constants (J) are given in Hz, and splitting patterns are designated as follows: bs, broad singlet; d, doublet; t, triplet; q, quartet; m, multiplet. Mass spectra were collected on a Brucker ESQUIRE electrospray/ion trap instrument in the positive and negative modes. Routine thin-layer chromatography (TLC) was performed on silica gel plates (Analtech, Inc., 250 microns). Flash chromatography was conducted on silica gel (Merck, grade 60, 230-400 mesh).

TABLE 1

| Compound | LogP | LPA₁ $I_{max}$ (%) | LPA₁ $EC_{50}$ (μM) | LPA₂ $I_{max}$ (%) | LPA₂ $EC_{50}$ (μM) | LPA₃ $I_{max}$ (%) | LPA₃ $EC_{50}$ (μM) | LPA₄ $I_{max}$ (%) | LPA₄ $EC_{50}$ (μM) | LPA₅ $I_{max}$ (%) | LPA₅ $EC_{50}$ (μM) | GPR87 $I_{max}$ (%) | GPR87 $EC_{50}$ (μM) | P2Y10 $I_{max}$ (%) | P2Y10 $EC_{50}$ (μM) |
|---|---|---|---|---|---|---|---|---|---|---|---|---|---|---|---|
| LPA 18:1 | 6.12 | | 0.13 | | 0.030 | | 0.080 | | 0.25 | | 0.015 | | 0.049 | | 0.029 |
| OTP | 7.72 | | 0.651 | | 0.336 | | 0.297 | | 2.0 | | 0.003 | | 3.0 | ND | ND |
| NSC 12404 | 3.25 | NE | NE | — | 9.5 | 61 | — | NE | NE | NE | NE | NE | NE | NE | NE |
| GRI 977143 | 3.88 | NE | NE | — | 3.3 | 55 | — | NE | NE | NE | NE | NE | NE | NE | NE |
| H2L 5547924 | 4.36 | 21 | — | — | 2.8 | 66 | — | 51 | — | NE | NE | 31 | — | 34 | — |
| H2L 5828102 | 2.78 | 29 | — | — | 3.3 | 100 (K = 1.5) | — | NE | NE | NE | NE | 21 | — | 39 | — |

Figure 13:
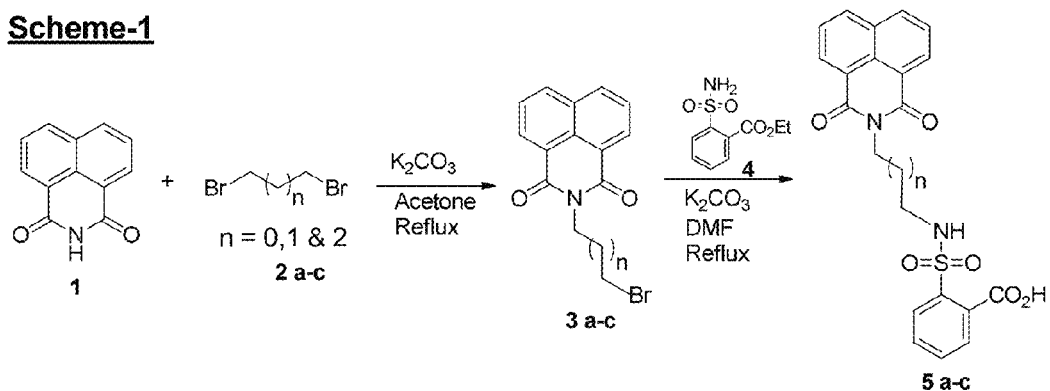
FIG. 13 is a series of three schemes for synthesis of compounds of the invention.
Figure 13:
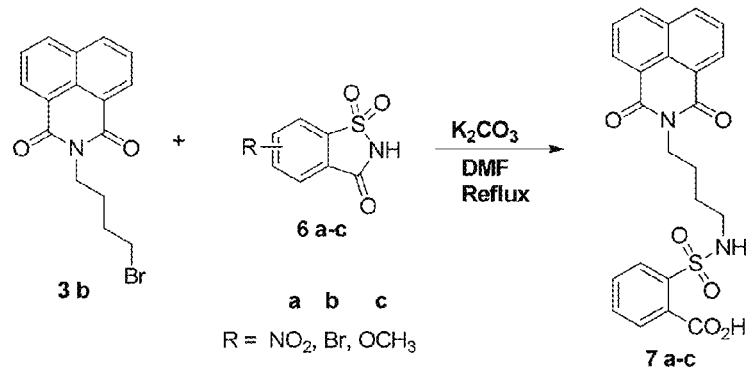
Figure 13:
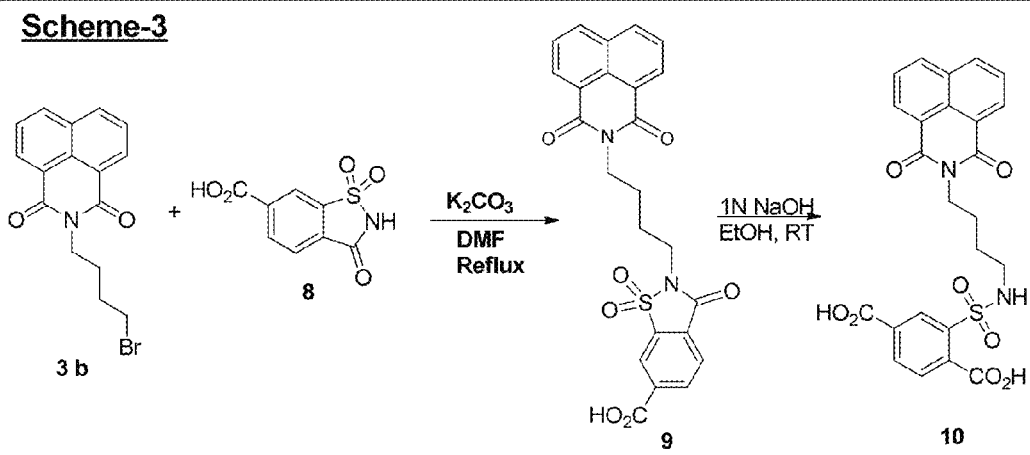
Figure 14:
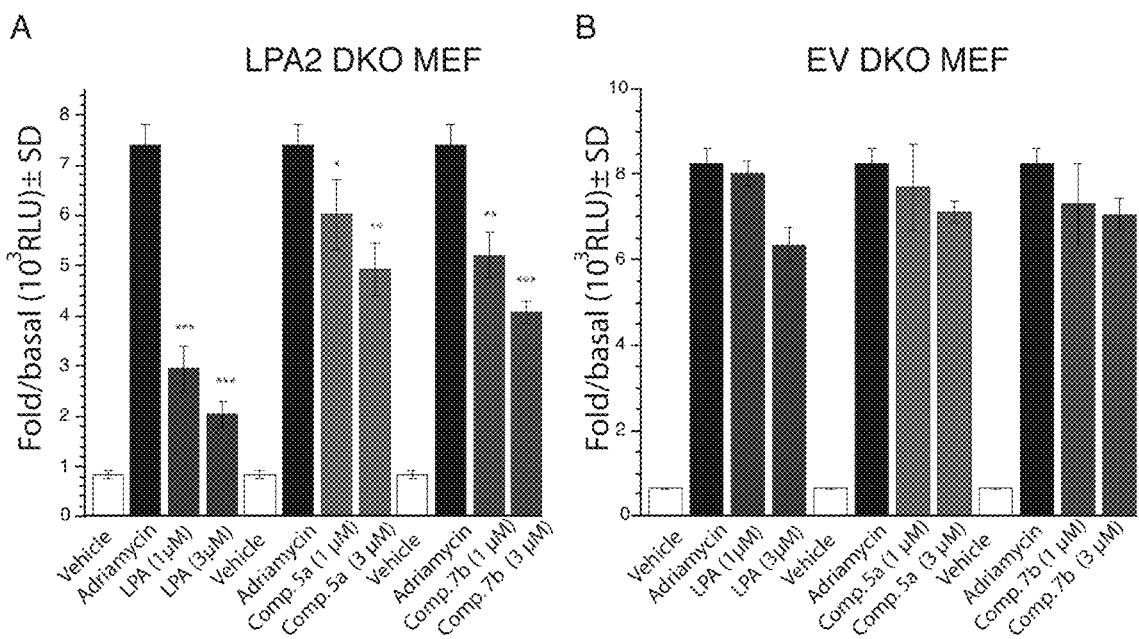
FIGS. 14A and 14B are bar graphs illustrating inhibition of caspase-3/7 activation in LPA2 DKO MEF cells (A) and in EV DKO MEF (B). LPA (1-3 µM), compound 5a (1-3 µM) and compound 7b (1-3 µM) were added to the cells 1 h before treatment with Adriamycin. Pretreatment with compounds 5a and 7b significantly reduced apoptosis in LPA2 DKO MEF cells but not in EV DKO MEF cells (*$p \leq 0.05$; $p \leq 0.01$; *$p \leq 0.001$).
Figure 15:
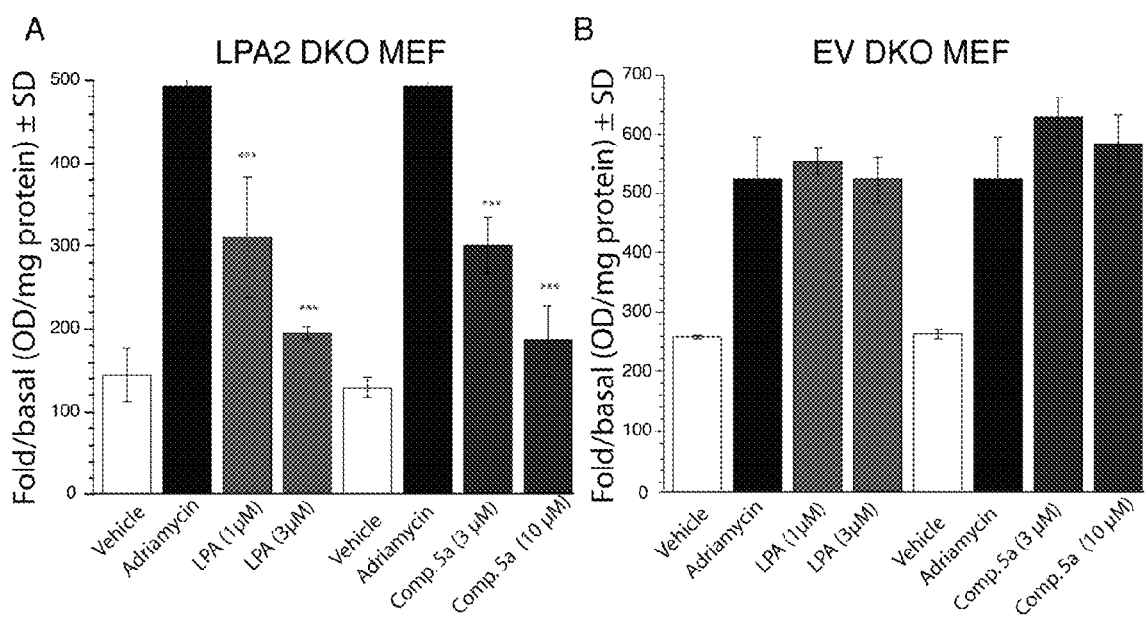
FIGS. 15A and 15B are bar graphs illustrating the effect of LPA (1-3 µM) and compound 5a (3-10 µM) on DNA fragmentation in LPA2 DKO MEF and in EV DKO MEF cells. Compound 5a at 3 µM concentration selectively protected LPA2 transduced cells from Adriamycin induced DNA fragmentation (***$p \leq 0.001$). 60 min pretreatment with 10 µM reduced DNA fragmentation by close to 50% percent in LPA2 DKO MEF cells. There was no protection in EV DKO MEF cells.
Figure 16:
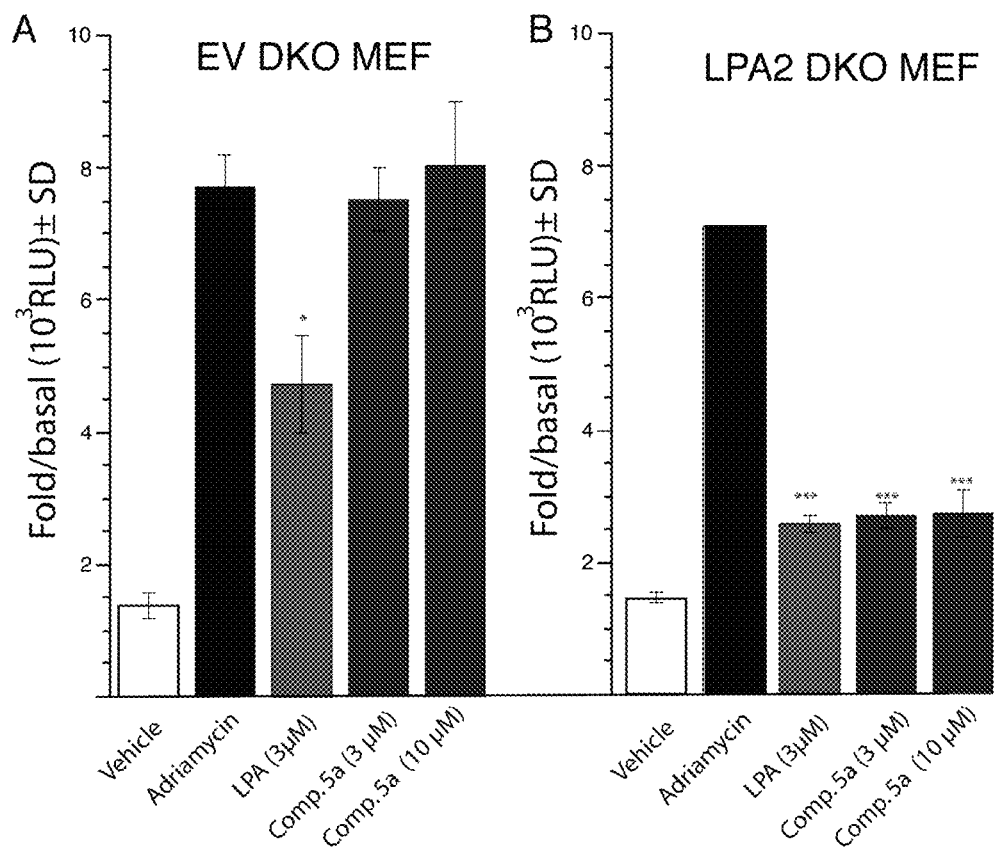
FIGS. 16A and 16B are bar graphs illustrating inhibition of the initiator caspase 8 in LPA2 DKO MEF cells and in empty vector DKO MEF cells LPA (3 µM), compound 5a (3-10 µM) were added to the cells 1 h before Adriamycin treatment.
Figure 17:
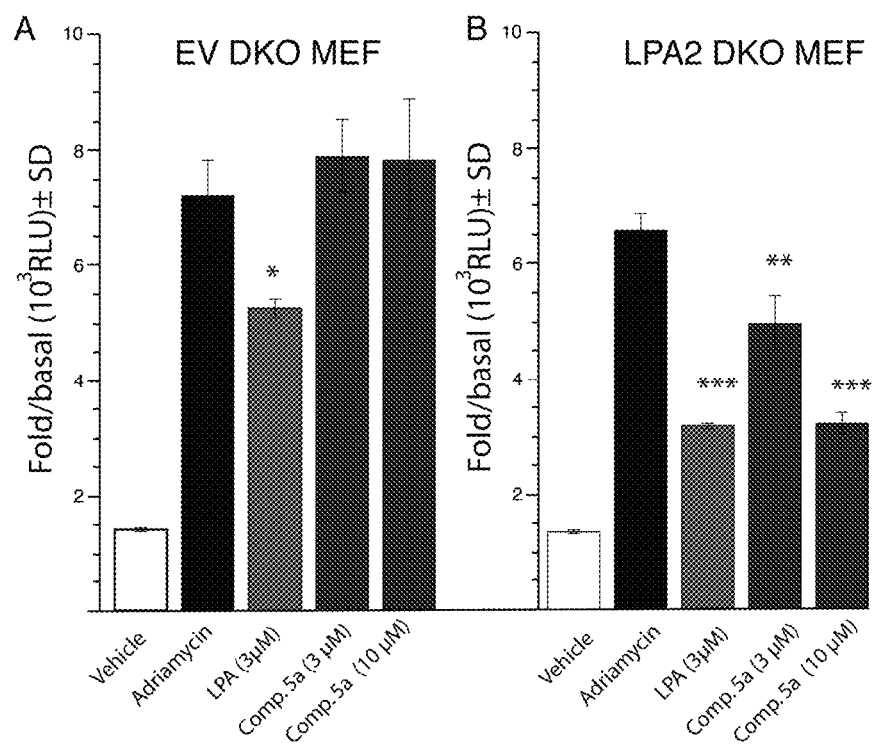
FIGS. 17A and 17B are bar graphs illustrating inhibition of the initiator caspase 9 in LPA2 DKO MEF cells and in empty vector DKO MEF cells LPA (3 µM), compound 5a (3-10 µM) were added to the cells 1 h before Adriamycin treatment.
Figure 18:
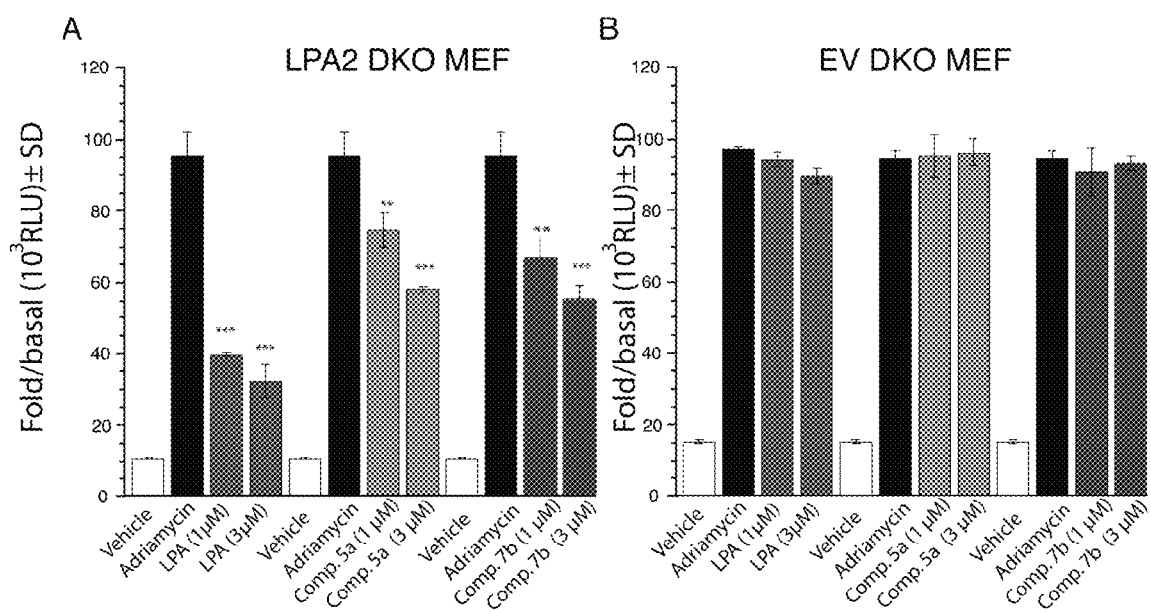
FIGS. 18A and 18B are bar graphs illustrating inhibition of executioner caspases 3 and 7 by LPA, compound 5a and 7b in LPA2 DKO MEF cells (A) and in vector transduced cells (B). Protective compounds were added to the cells 1 h after irradiation with 15 Gy and caspase 3,7 activation was measured 4 h after irradiation. (***$p \leq 0.001$ compared to irradiated vehicle.
Figure 19:
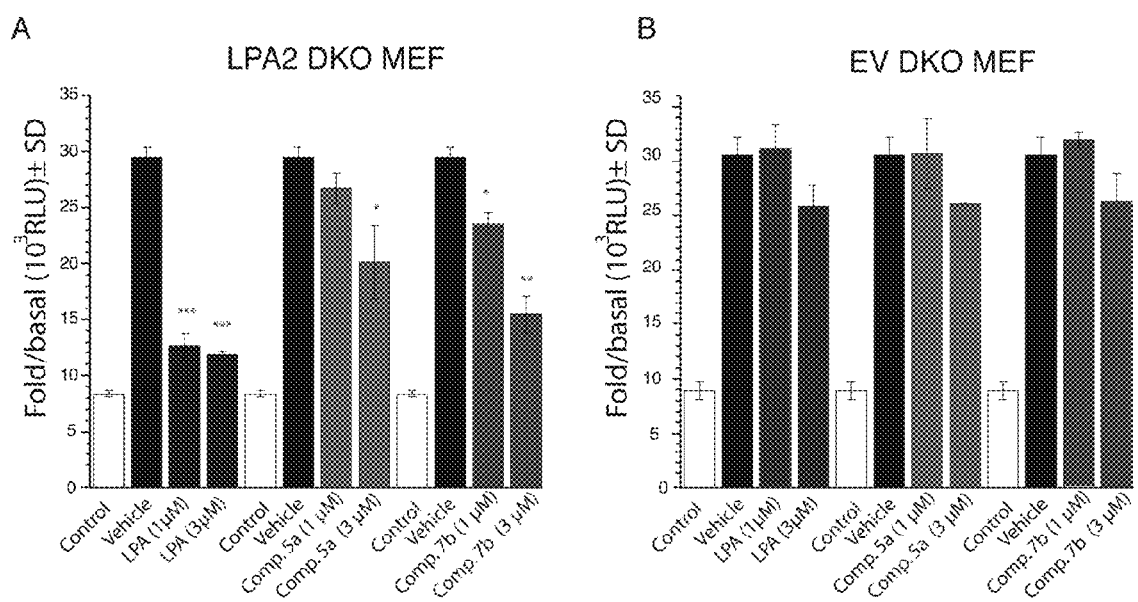
FIGS. 19A and 19B are bar graphs illustrating inhibition of the initiator caspase 9 in LPA2 DKO MEF cells (A) and in empty vector DKO MEF cells (B) (*$p < 0.05$; $p < 0.01$; *$p < 0.001$). Protective compounds LPA (1-3 µM), 5a and 7b (1-3 µM) were added to the cells 1 h after γ-irradiation with 15 Gy and DNA fragmentation was measured 4 hours after irradiation (**-$p \leq 0.001$), compared to irradiated vehicle.

The inventors then designed and synthesized novel sulfamoyl benzoic acid derivatives, compounds 5a-c, 7a-c, 9 and 10 as shown in Schemes 1, 2, and 3, respectively, of FIG. 13. Compounds 3a-c were prepared by modification of a previously-reported procedure. Briefly, formation of compounds 3a-c was accomplished by the reaction of benzo[de]isoquinoline-1,3-dione (1) and corresponding dibromoalkanes (2a-c) in presence of K₂CO₃/acetone under reflux conditions in quantitative yield. The compound 3a-c was reacted with 2-sulfamoylbenzoic acid ethyl ester 4 in K₂CO₃/DMF and furnished compound 5a-c in moderate yield (Scheme 1). The reaction of 2-(4-bromobutyl)benzo[de]isoquinoline-1,3-dione (3b) with substituted benzo[d]isothiazol-3(2H)-one-1,1-dioxides 6a-c and 8 in the presence of K₂CO₃ and DMF produced compounds 7a-c and 9, respectively (Schemes 2 and 3). Compound 9 was treated with aqueous 1N NaOH in EtOH gave the final compound 10 (Scheme 3).

The newly-synthesized compounds were tested for their ability to induce Ca²⁺ transients in RH7777 cells stably expressing the LPA₂ receptor. The effect of these new compounds (5a-c, 7a-c, 9 and 10) on the activity of LPA₂ receptor is shown in Table 2.

TABLE 2

| Compound | Carbon linker | Log P | $EC_{50}$ (μM); Emax (%) (RH7777) | $EC_{50}$ (μM); Emax (%) (DKO MEF) |
|---|---|---|---|---|
| GRI-977143 | 3 | 3.88 | 3.3; 64 | ND |
| 5a | 3 | 2.7 | 2.2; 100 | ND |
| 5b | 4 | 3.16 | 0.5; 100 | 0.5; 100 |
| 5c | 5 | 3.62 | 1.2; 100 | ND |
| 7a | 4 | 3.12 | >10 | >10 |
| 7b | 4 | 4.05 | 1; 100 | 0.4; 100 |
| 7c | 4 | 3.29 | >10 | ND |
| 9 | 4 | 2.74 | 3.6; 75 | ND |
| 10 | 4 | 2.52 | NE | NE |

All reagents and solvents were purchased from Aldrich, Alfa-Aesar, Chemgenx Product List, Matrix Scientific, and TCI-America Fine Chemicals, and used without further purification. The reactions were performed under an inert atmosphere of argon. ¹H-NMR spectra were recorded on a Bruker ARX 400 and Varian 500 spectrometer at 400 MHz and 500 MHz, respectively and were referenced to internal (CH₃)₄Si.

2-(bromoalkyl)benzo[de]isoquinoline-1,3-dione (3a-c) (GP-1)

To a solution of benzo[de]isoquinoline-1,3-dione 1 (1 equiv) in dry acetone were added anhydrous K₂CO₃ (3 equiv) and corresponding dibromoalkane (2a-c) (3 equiv). The reaction mixture was refluxed for 22 h, cooled to room temperature and filtered. The solvent was evaporated under reduced pressure and the crude product was purified by flash column chromatography to afford the title compound.

2-[3-(1,3-dioxo-1H,3H-benzo[de]isoquinolin-2-yl)-alkylsulfamoyl]benzoic acid (5a-c) (GP-2)

To a stirred mixture of 2-sulfamoylbenzoic acid ethyl ester 4 (1 equiv) and anhydrous K₂CO₃ (5 equiv) in DMF was added 2-(bromoalkyl)benzo[de]isoquinoline-1,3-dione (3a-c) (3 equiv). The reaction mixture was gently refluxed for overnight, cooled to room temperature and poured into the crushed ice. The resulted solution was acidified with concentrated HCl and extracted with chloroform. The organic layer was washed with water, dried over anhydrous Na₂SO₄ and concentrated under vacuum to get the crude product. The Crude residue was purified by flash column chromatography to obtain the desired product.

2-(N-(4-(1,3-dioxo-1H-benzo[de]isoquinolin-2(3H)-yl)butyl)sulfamoyl)-4-substituted benzoic acid (7a-c) (GP-3)

To a stirred mixture of 6-substituted benzo[d]isothiazol-3 (2H)-one 1,1-dioxide 6a-c (1 equiv) and anhydrous K₂CO₃ (5 equiv) in DMF was added 2-(4-bromobutyl)-1H-benzo[de] isoquinoline-1,3(2H)-dione (3b) (3 equiv). The reaction mixture was gently refluxed for overnight, cooled to room temperature and poured into the crushed ice. The resulted solution was acidified with con. HCl and extracted with chloroform. The organic layer was washed with water, dried over anhydrous Na₂SO₄ and concentrated under vacuum to get the crude product. The Crude product was purified by flash column chromatography to afford the title product.

2-(3-Bromopropyl)benzo[de]isoquinoline-1,3-dione (3a)

This compound was prepared according to GP-1 using benzo[de]isoquinoline-1,3-dione (1) and 1,2 dibromopropane (2a) The crude product was purified by flash column chromatography using EtOAc-hexane to provide 3a. $^1$H NMR (500 MHz, CDCl$_3$) δ 8.62 (d, J=7.0 Hz 2H), 8.23 (d, J=8.0 Hz, 2H), 7.77 (t, J=7.5 Hz, 2H), 4.34 (t, J=7.5, 2H), 3.51 (t, J=7.0 Hz, 2H), 2.37-2.32 (m, 2H). MS (ES+) m/z 340 (M+Na)$^+$.

2-(4-Bromobutyl)benzo[de]isoquinoline-1,3-dione (3b)

This compound was prepared according to GP-1 using benzo[de]isoquinoline-1,3-dione (1) and 1,2 dibromobuane (2b) The crude residue was purified by flash column chromatography using EtOAc-hexane to get 3b. $^1$H NMR (500 MHz, CDCl$_3$) δ 8.61 (d, J=7.5 Hz 2H), 8.22 (d, J=8.5 Hz, 2H), 7.77 (t, J=7.5 Hz, 2H), 4.34 (t, J=7.5, 2H), 3.49 (t, J=7.0 Hz, 2H), 2.03-1.91 (m, 4H). MS (ES+) m/z 354 (M+Na)$^+$.

2-(5-Bromopentyl)benzo[de]isoquinoline-1,3-dione (3c)

This compound was prepared according to GP-1 using benzo[de]isoquinoline-1,3-dione (1) and 1,2 dibromopentane (2c) The crude product was purified by flash column chromatography using EtOAc-hexane to give 3c. $^1$H NMR (500 MHz, CDCl$_3$) δ 8.63 (d, J=7.5 Hz 2H), 8.24 (d, J=8.0 Hz, 2H), 7.78 (t, J=7.5 Hz, 2H), 4.22 (t, J=7.0, 2H), 3.45 (t, J=7.0 Hz, 2H), 2.01-1.94 (m, 2H), 1.84-1.78 (m, 2H), 1.64-1.57 (m, 2H), MS (ES+) m/z 368 (M+Na)$^+$.

2-[3-(1,3-Dioxo-1H,3H-benzo[de]isoquinolin-2-yl) propylsulfamoyl]benzoic acid (5a)

The compound was prepared according to GP-2 using 2-sulfamoylbenzoic acid ethyl ester 4 and compound 3a. The crude product was purified by flash column chromatography using MeOH—CHCl$_3$ to obtain 5a. $^1$H NMR (500 MHz, DMSO-d$_6$) δ 9.43 (bs, 2H), 8.49-8.46 (m, 4H), 7.87 (t, J=8.0 Hz, 2H), 7.68 (d, J=7.5 Hz 1H), 7.64 (d, J=8.0 Hz 1H), 7.49 (t, J=7.5 Hz, 1H), 7.33 (t, J=7.5 Hz, 1H), 4.02 (t, J=7.5, 2H), 2.76 (q, J=7.0 Hz, 2H), 1.90-1.60 (m, 2H). MS (ES-) m/z 437 (M-H)$^-$.

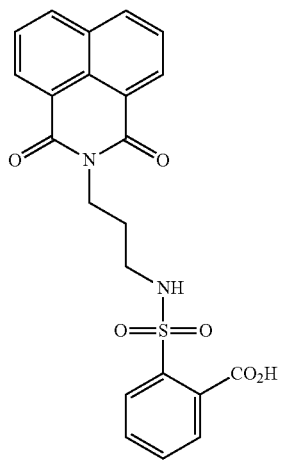

5a

2-[4-(1,3-Dioxo-1H,3H-benzo[de]isoquinolin-2-yl) butylsulfamoyl]benzoic acid (5b)

The compound was prepared according to GP-2 using 2-sulfamoylbenzoic acid ethyl ester 4 and compound 3b. The crude product was purified by flash column chromatography using MeOH—CHCl$_3$ to obtain 5b. $^1$H NMR (500 MHz, DMSO-d$_6$) δ 9.27 (bs, 2H), 8.49-8.45 (m, 4H), 7.87 (t, J=8.0 Hz, 2H), 7.69 (d, J=8.0 Hz 1H), 7.63 (d, J=8.0 Hz 1H), 7.44 (t, J=7.5 Hz, 1H), 7.32 (t, J=7.5 Hz, 1H), 3.99 (t, J=7.0, 2H), 2.71 (q, J=7.0 Hz, 2H), 1.64-1.56 (m, 2H), 1.46-1.38 (m, 2H). MS (ES-) m/z 451 (M-H)$^-$.

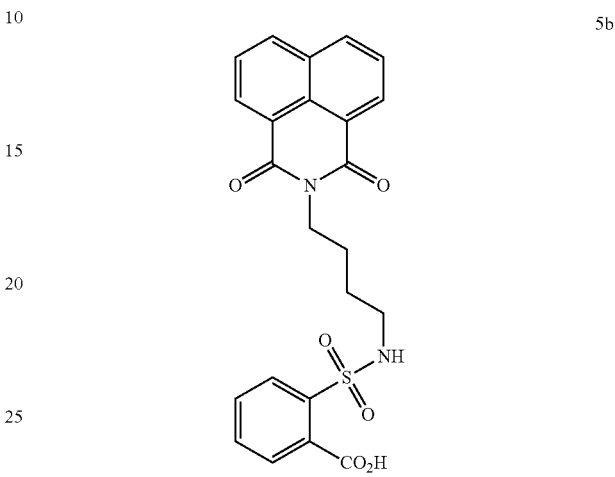

5b

2-[4-(1,3-Dioxo-1H,3H-benzo[de]isoquinolin-2-yl pentylsulfamoyl]benzoic acid (5c)

The compound was prepared according to GP-2 using 2-sulfamoylbenzoic acid ethyl ester 4 and compound 3c. The crude residue was purified by flash column chromatography using MeOH—CHCl$_3$ to obtain 5c. $^1$H NMR (400 MHz, DMSO-d$_6$) δ 9.17 (bs, 2H), 8.50-8.45 (m, 4H), 7.89-7.85 (m, 2H), 7.72 (d, J=10.0 Hz 1H), 7.66 (d, J=10.0 Hz 1H), 7.51 (t, J=10.0 Hz, 1H), 7.39 (t, J=10.0 Hz, 1H), 3.97 (t, J=9.5, 2H), 2.68 (q, J=8.0 Hz, 2H), 1.58-1.50 (m, 2H), 1.44-1.38 (m, 2H), 1.33-1.26 (m, 2H). MS (ES-) m/z 465 (M-H)$^-$.

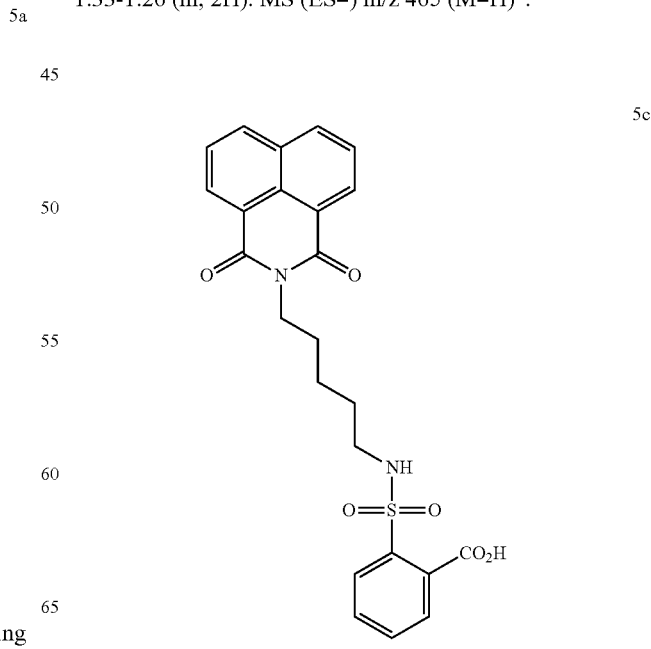

5c

2-(N-(4-(1,3-dioxo-1H-benzo[de]isoquinolin-2(3H)-yl)butyl)sulfamoyl)-4-nitrobenzoic acid (7a)

The compound was prepared according to GP-3 using 6-nitrobenzo[d]isothiazol-3(2H)-one 1,1-dioxide 6a. The crude residue was purified by flash column chromatography using MeOH—CHCl$_3$ to obtain 7a. $^1$H NMR (400 MHz, DMSO-d$_6$) δ 9.47 (t, J=5.6 Hz, 1H), 8.51-8.45 (m, 4H), 7.86-7.81 (m, 4H, 2H), 7.62 (d, J=8.4 Hz 1H), 7.26 (s, 1H), 7.01 (q, J=2.8 Hz, 1H), 3.95 (t, J=6.8 Hz, 2H), 2.83-2.72 (m, 2H), 1.62-1.65 (m, 2H), 1.50-1.38 (m, 2H). MS (ES−) m/z 496 (M−H)$^-$.

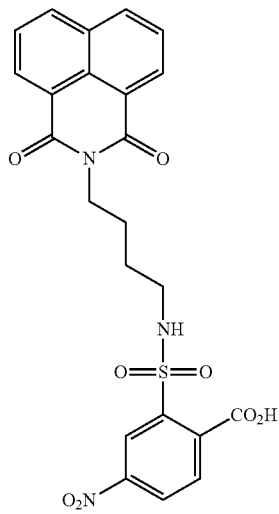

7a

4-bromo-2-(N-(4-(1,3-dioxo-1H-benzo[de]isoquinolin-2(3H)-yl)butyl)sulfamoyl) benzoic acid (7b)

The compound was prepared according to GP-3 using 6-bromobenzo[d]isothiazol-3(2H)-one 1,1-dioxide 6b. The crude residue was purified by flash column chromatography using MeOH—CHCl$_3$ to obtain 7b. $^1$H NMR (400 MHz, DMSO-d$_6$) δ 9.13 (t, J=5.2 Hz, 1H), 8.52-8.44 (m, 4H), 7.88 (t, J=8.0 Hz, 2H), 7.70 (d, J=7.6 Hz 1H), 7.60 (d, J=7.6 Hz 1H), 7.47-7.41 (m, 1H), 4.08 (t, J=7.6 Hz, 2H), 2.78-2.67 (m, 2H), 1.64-1.57 (m, 2H), 1.48-1.39 (m, 2H). MS (ES−) m/z 529 (M−H)$^-$.

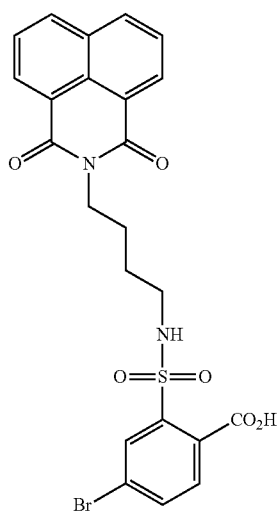

7b

2-(N-(4-(1,3-dioxo-1H-benzo[de]isoquinolin-2(3H)-yl)butyl)sulfamoyl)-4-methoxybenzoic acid (7c)

The compound was prepared according to GP-3 using 6-methoxybenzo[d]isothiazol-3(2H)-one 1,1-dioxide 6c. The crude residue was purified by flash column chromatography using MeOH—CHCl$_3$ to obtain 7c. $^1$H NMR (400 MHz, DMSO-d$_6$) δ 9.31 (t, J=5.2 Hz, 1H), 8.56-8.41 (m, 4H), 7.88 (t, J=8.0 Hz, 2H), 7.61 (d, J=8.0 Hz 1H), 7.37 (d, J=4.0 Hz, 1H), 6.95 (dd, J=2.8, 2.8 Hz, 1H), 4.08 (t, J=8.0 Hz, 2H), 3.79 (s, 3H), 3.24 (q, J=6.8 Hz, 2H), 1.77-1.69 (m, 2H), 1.60-1.52 (m, 2H). MS (ES −)m/z 481 (M−H)$^-$.

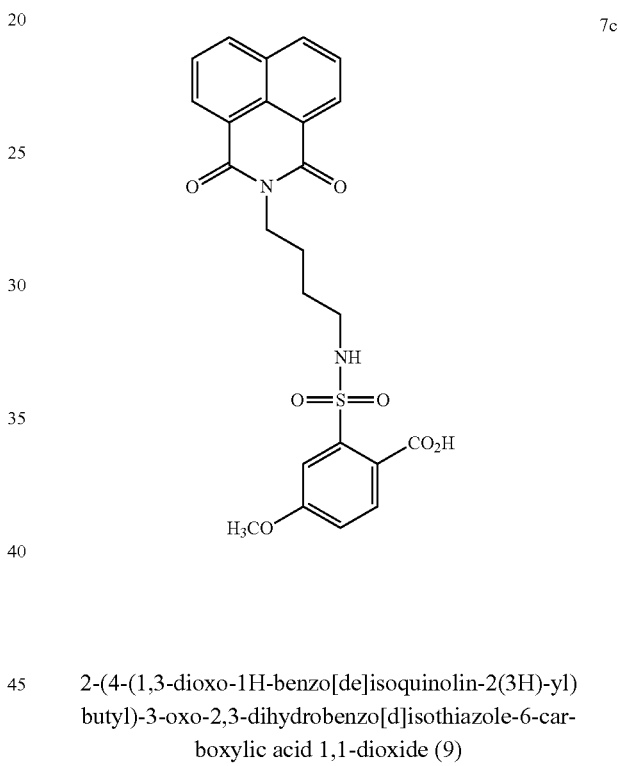

7c

2-(4-(1,3-dioxo-1H-benzo[de]isoquinolin-2(3H)-yl)butyl)-3-oxo-2,3-dihydrobenzo[d]isothiazole-6-carboxylic acid 1,1-dioxide (9)

To a stirred mixture of 3-oxo-2,3-dihydrobenzo[d]isothiazole-6-carboxylic acid 1,1-dioxide (8) (1 mmol) and anhydrous K$_2$CO$_3$ (5 mmol) in DMF was added 2-(4-bromobutyl)-1H-benzo[de]isoquinoline-1,3(2H)-dione (3b) (3 mmol). The reaction mixture was gently refluxed for overnight, cooled to room temperature and poured into the crushed ice. The resulted solution was acidified with con. HCl and extracted with ethylacetate. The organic layer was washed with water, dried over anhydrous Na$_2$SO$_4$ and concentrated under vacuum to get the crude product. The Crude residue was purified by flash column chromatography using MeOH—CHCl$_3$ (2:8) to obtain the desired product. $^1$H NMR (400 MHz, DMSO-d$_6$) δ 8.54-8.34 (m, 6H), 7.91-7.77 (m, 3H), 4.41-4.37 (m, 2H), 4.14-4.08 (m, 2H), 1.89-1.71 (m, 4H). MS (ES−) m/z 477 (M−H)$^-$.

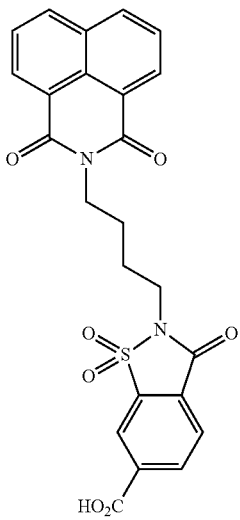

2-(N-(4-(1,3-dioxo-1H-benzo[de]isoquinolin-2(3H)-yl)butyl)sulfamoyl)terephthalic acid (10)

A suspension of 9 (50 mg) and aqueous 1N NaOH (3 mL) was stirred at room temperature for 10 min. To this suspension, ethanol (2 mL) was added until the solution became clear. Stirring was continued for 2 h until starting material was disappeared. The solution was poured into ice-water and acidified with 37% HCl to a pH of 1. The resulted mass was extracted with ethylacetate, the organic layer was washed with water, dried over anhydrous $Na_2SO_4$ and concentrated under vacuum to get the crude product. The crude residue was recrystallized using EtOAc-Hexane-DCM to afford the title compound. $^1$H NMR (400 MHz, DMSO-$d_6$) δ 13.5 (bs, 1H), 9.30 (bs, 1H), 8.58-8.35 (m, 4H), 8.05 (d, J=8.0 Hz, 1H), 7.99-7.86 (m, 2H), 7.65-7.52 (m, 2H), 4.01-3.97 (m, 2H), 3.50-3.40 (m, 2H), 1.52-1.40 (m, 4H). MS (ES−) m/z 495 (M−H)$^-$.

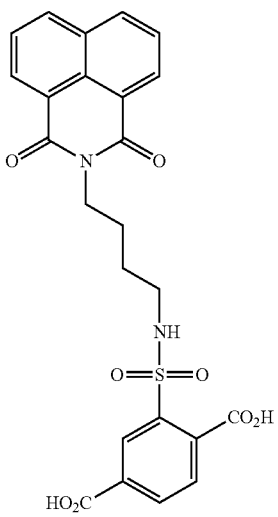

10

LPA receptor agonists and antagonists of the present invention may be used to prepare pharmaceutical compositions suitable for treatment of patients. Therefore, a further aspect of the present invention relates to a pharmaceutical composition that includes a pharmaceutically-acceptable carrier and a compound of the present invention. The pharmaceutical composition can also include suitable excipients, or stabilizers, and can be in solid or liquid form such as, tablets, capsules, powders, solutions, suspensions, or emulsions. Typically, the composition will contain from about 0.01 to 99 percent, preferably from about 20 to 75 percent of active compound(s), together with the carrier, excipient, stabilizer, etc.

The solid unit dosage forms can be of the conventional type. The solid form can be a capsule, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The compounds of the present invention may also be administered in injectable or topically-applied dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carrier, including adjuvants, excipients or stabilizers. Oils may be those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Depending upon the treatment being effected, the compounds of the present invention can be administered orally, topically, transdermally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes.

Determination of optimal ranges of effective amounts of each component is within the skill of the art. Treatment regimens for the administration of the compounds of the present invention can also be determined readily by those with ordinary skill in art, given the disclosure provided herein by the inventors.

The invention may be further described by means of the following non-limiting examples.

EXAMPLES

Lysophosphatidic acid (18:1) was purchased from Avanti Polar Lipids (Alabaster, Ala.). OTP was synthesized and provided by RxBio, Inc. (Johnson City, Tenn.) as described (Durgam et al., 2006). The test compounds used in the present study were obtained from the following vendors: Genome Research Institute (GRI) GRI977143 from the University of Cincinnati Drug Discovery Center (UC-DDC; Cincinnati, Ohio); Hit2Lead (www.hit2lead.com) H2L5547924, and H2L5828102, from ChemBridge (San Diego, Calif.); and NSC12404 from the National Cancer Institute Developmental Therapeutics Program Open Chemical Repository. Ten mM stock solutions of GRI977143, H2L5547924, H2L5828102, and NSC12404 were prepared in dimethyl sulfoxide (DMSO). One millimolar stocks of LPA and OTP as an equimolar complex of charcoal-stripped, fatty acid-free bovine serum albumin (BSA) (Sigma-Aldrich) St. Louis, Mo.) were prepared just before use in phosphate-buffered saline (PBS). A stock solution of 3.45 mM Adriamycin was prepared in distilled water.

Computational Docking

Compounds were flexibly docked into the activated $LPA_2$ receptor homology model reported by Sardar et al. (Sardar et al., Molecular basis for lysophosphatidic acid receptor antagonist selectivity. *Biochim Biophys Acta* (2002) 1582(1-3): 309-317) using Autodock Vina (Trott and Olson, AutoDock Vina: improving the speed and accuracy of docking with a new scoring function, efficient optimization, and multithreading. *J. Comput. Chem.* (2010) 31(2): 455-461). The compounds and receptor homology model were both energy optimized with the Merck Molecular Force Field 94 (MMFF94) in the Molecular Operating Environment software (MOE, 2010.10 version) prior to docking. Docking simulations were performed using a docking box with dimensions of 65×63×50 Å and a search space of 20 binding modes, and an exhaustive search parameter was set at 5. The best docking pose was chosen based on the lowest energy conformation. Finally, the best pose was further refined using the MMFF94 in MOE.

Ligand-Based Similarity Search

Similarity searching of NSC12404 was performed using the UC-DDC library database (drugdiscovery.uc.edu). The Tanimoto similarity indices for the reference compounds were calculated using ECFC6, FCFP4, and FCFP6 fingerprints in Pipeline Pilot software (Accelerys, Inc.; San Diego, Calif.). The UC-DCC library was screened using Pipeline Pilot fingerprints to identify additional $LPA_2$ ligands. A similarity threshold was set at 80%. Among the 225 returned hits, compounds with similarity >80% were selected by visual inspection, carefully considering the similarity and how closely the structures reflected the reference compound. A total of 27 compounds was selected for evaluation using LPA receptor-activated $Ca^{2+}$-mobilization assays.

Residue Nomenclature

Amino acids in the transmembrane (TM) domains were assigned index positions to facilitate comparison between GPCRs with different numbers of amino acids, as described by Ballesteros and Weinstein (Ballesteros and Weinstein, Integrated methods for the construction of three dimensional models and computational probing of structure-function relations in G-protein coupled receptors. *Methods Neurosci* (1995) 25: 366-425). An index position is in the format X.YY., where X denotes the TM domain in which the residue appears, and YY indicates the position of that residue relative to the most highly conserved residue in that TM domain, which is arbitrarily assigned position 50.

LPA receptor-mediated $Ca^{2+}$ mobilization assay

Stable cell lines expressing the individual $LPA_1$, $LPA_2$, $LPA_3$, $LPA_4$, and $LPA_5$ established receptor subtypes, as well as putative LPA receptors GPR87 and P2Y10, or appropriate empty vector-transfected controls have been previously generated and described (Murakami et al., Identification of the orphan GPCR, P2Y(10) receptor as the sphingosine-1-phosphate and lysophosphatidic acid receptor. *Biochem Biophys Res Commun* (2008) 371(4): 707-712; Tabata et al., The orphan GPCR GPR87 was deorphanized and shown to be a lysophosphatidic acid receptor. *Biochem Biophys Res Commun* (2007) 363(3): 861-866; Williams et al., Unique ligand selectivity of the GPR92/LPA5 lysophosphatidate receptor indicates role in human platelet activation. *J Biol Chem* (2009) 284(25): 17304-17319). Assays for ligand-activated mobilization of intracellular $Ca^{2+}$ were performed using a Flex Station 2 robotic fluorescent plate reader (Molecular Devices; Sunnyvale, Calif.) as previously described (Durgam et al., Synthesis and pharmacological evaluation of second-generation phosphatidic acid derivatives as lysophosphatidic acid receptor ligands. *Bioorg Med Chem Lett* (2006) 16(3): 633-640). The appropriate concentrations of the test compounds were either used alone (for agonist testing) or mixed with the respective ~$EC_{75}$ concentration of LPA 18:1 for the LPA receptor being tested (antagonist screen). The cells were loaded with Fura-2-acetoxymethyl esther (Fura-2/AM) in Krebs buffer containing 0.01% pluronic acid for 30 min and rinsed with Krebs buffer before measuring $Ca^{2+}$ mobilization. The ratio of peak emissions at 510 nm after 2 min of ligand addition was determined for excitation wavelengths of 340 nm/380 nm. All samples were run in quadruplicate. The inhibition elicited by 10 μM test compound on the $EC_{75}$ concentration of LPA 18:1 for a given receptor ($I_{10\mu m}$) was interpolated from the dose-response curves. The half maximally effective concentration ($EC_{50}$), and inhibitory constant ($K_i$) values were calculated by fitting a sigmoid function to dose-response data points using KaleidaGraph software (version 4.1, Synergy Software; Dubai, United Arab Emirates).

Cell Culture

Mouse embryonic fibroblast (MEF) cells were isolated from E13.5 $LPA_{1\&2}$ double knockout (DKO) embryos. MEFs were transduced with empty vector or $LPA_2$-containing lentiviruses and selected with 1.5 μg/ml puromycin. Cells were maintained in Dulbecco's modified Eagle medium (DMEM) supplemented with 10% (V/V) fetal bovine serum (FBS), 2 mM L-glutamine, 100 U/mL penicillin, and 100 μg/mL streptomycin. Serum-free medium contained 0.1% (W/V) BSA in DMEM. The rat intestinal epithelial cell line 6 (IEC-6) was obtained from the American Type Culture Collection (Rockville, Md.) at passage 13; passages 16-21 were used in all experiments. IEC-6 cells were maintained in a humidified 37° C. incubator in an atmosphere of 90% air and 10% $CO_2$. Growth medium consisted of DMEM supplemented with 5% heat inactivated FBS, 10 μg/mL insulin, and 50 μg/mL gentamycin. The composition of the serum-starvation medium was the same as that of the full growth medium except that it contained no FBS. The McArdle rat hepatoma cell line (RH7777) stably expressing $LPA_2$ receptors was a gift from Dr. Fumikazu Okajima (Gunma University, Maebashi, Japan). RH7777 cells stably expressing $LPA_1$ or $LPA_3$ receptors were generated in-house and had been characterized earlier. Wild type and LPA receptor (LPAR) stably transfected RH7777 cells were grown in DMEM supplemented with 10% FBS and 2 mM L-glutamine in the presence of 250 μg/ml G418. Chinese hamster ovary (CHO) cells stably expressing either vector or $LPA_4$ receptor were a kind gift from Dr. Takao Shimizu (Tokyo University; Tokyo, Japan). Cells were cultured in Ham's F12 medium containing 10% FBS, 2 mM L-glutamine, and 350 μg/ml G418. Rat neuroblastoma cells (B103) were transduced with the lentivirus harboring wild type of FLAG-$LPA_5$ and selected with puromycin to establish the stable cell lines. The stable cells were maintained in DMEM supplemented with 10% FBS and 0.4 μg/ml puromycin. GPR87- and P2Y10-expressing CHO cells and vector-transfected control cells were a gift from Dr. Norihisha Fujita (Ritsumeikan University; Shiga, Japan). The highly invasive MM1 rat hepatoma cells (gift from Dr. Michiko Mukai, Osaka University, Japan) were grown in suspension in DMEM supplemented with 10% (V/V) FBS, 2 mM L-glutamine, 100 U/mL penicillin, and 100 μg/mL streptomycin. Human umbilical vein endothelial cells (HUVEC) were purchased from VEC Technologies Inc. (Rensselaer, N.Y., USA) and cultured in MCDB-131 complete medium supplemented with 10% (V/V) FBS, 90 μg/mL heparin, 10 ng/mL EGF, 1 μg/mL hydrocortisone, 0.2 mg/mL Endo- Growth (VEC Technologies Inc.) supplement, 100 U/mL penicillin G, 100 µg/mL streptomycin, and 25 µg/mL amphotericin B.

Cell Proliferation Assay

For determination of the effect of the LPA receptor ligands on cell growth, vector- and $LPA_2$-transduced MEF cells ($2\times10^4$) were plated in each well of a 24-well plate in full growth medium. Cells were counted the next day and the medium was replaced with medium containing 1.5% (V/V) FBS supplemented with or without 1 µM LPA, 1 µM OTP, or 10 µM GRI977143. Media containing LPA, OTP, and GRI977143 were refreshed every 24 h. The growth rate was measured by counting the number of cells in triplicate using the Z1 Coulter Particle Counter (Beckman Coulter; Hileah, Fla.) as a function of time.

Induction of Apoptosis by Adriamycin or Serum Withdrawal

Experiments were performed on vector- and $LPA_2$-transduced MEF cells. To measure caspase 3, 7, 8, or 9 activity and DNA fragmentation, cells were plated in 48-well plates ($2\times10^4$ cells/well). To detect PARP-1 cleavage and Bax translocation, $1.5\times10^6$ cells were plated in 10-cm dishes and cultured overnight in full growth medium. The next morning, the growth medium was replaced by serum-starvation medium and cells were pretreated for 1 h with LPA (1-10 µM), OTP (1-10 µM), GRI977143 (1-10 µM), or vehicle. Caspase activity, DNA fragmentation, PARP-1 cleavage, and Bax translocation were measured 5 h after incubation with 1.7 µM Adriamycin or 24 h after serum withdrawal.

Induction of Apoptosis by Tumor Necrosis Factor α (TNF-α) in IEC-6 Cells

Confluent serum-starved IEC-6 cells were treated with or without TNF-α (10 ng/ml)/cycloheximide (CHX) (20 µg/ml) in the presence of OTP (10 µM), GRI977143 (10 µM), or LPA (1 µM) for 3 h. Cells were washed twice with PBS and the quantitative DNA fragmentation assay was carried out as described previously (Valentine et al., (S)—FTY720-vinylphosphonate, an analogue of the immunosuppressive agent FTY720, is a pan-antagonist of sphingosine 1-phosphate GPCR signaling and inhibits autotaxin activity. *Cell Signal* (2010) 22(10): 1543-1553).

Caspase Activity Assay

Caspase-Glow® 3/7, Caspase-Glow® 8 and Caspase-Glow® 9 reagents were purchased from Promega (Madison, Wis.) and used according to the manufacturer's instructions. Briefly, cells were lysed by adding 50 µl of lysis reagent per well, followed by shaking for 30 min at room temperature. Two hundred µl lysate were transferred to a 96-well white-wall plate, and luminescence was measured using a BioTek® (Winooski, Vt.) plate reader.

DNA Fragmentation ELISA

Apoptotically-challenged cells were washed twice with PBS, and a quantitative DNA fragmentation assay was carried out using a Cell Death Detection ELISA PLUS kit (Roche Diagnostics, Penzberg, Germany) and normalized to protein concentration using the BCA Protein Assay Kit (Thermo Fisher Scientific, Inc.; Rockford, Ill.) as described previously (Valentine et al., 2010). Aliquots of nuclei-free cell lysate were placed in streptavidin-coated wells and incubated with anti-histone-biotin antibody and anti-DNA peroxidase-conjugated antibody for 2 h at room temperature. After the incubation, the sample was removed, and the wells were washed and incubated with 100 µl 2,2'-azino-di[3-ethylbenzthiazolin-sulfonate substrate at room temperature before the absorbance was read at 405 nm. Results were expressed as absorbance at 405 nm/min/mg protein as detailed in our previous report (Ray et al., Mdm2 inhibition induces apoptosis in p53 deficient human colon cancer cells by activating p73- and E2F1-mediated expression of PUMA and Siva-1. *Apoptosis* (2011) 16(1): 35-44).

MM1 Hepatoma Cell Invasion of Endothelial Monolayer

HUVEC ($1.3\times10^5$ cells at passages 5 to 7) were seeded into each well of a 12-well plate pre-coated with 0.2% gelatin (Sigma-Aldrich). Cells were grown for two days until a confluent monolayer was formed. MM1 cells were pre-labeled with 2 µg/mL calcein AM (Life Technologies; Grand Island, N.Y.) for 2 h and rinsed twice, and $5\times10^4$ cells per well were seeded over the HUVEC monolayer. Tumor-monolayer cell invasion was carried out for 20 h in MCDB-131 complete media containing 1% FBS with or without the addition of 1 µM LPA or 1-10 µM GRI977143. Non-invaded tumor cells were removed by repeatedly rinsing the monolayer with PBS (containing $Ca^{2+}$ and $Mg^{2+}$), followed by fixation with 10% buffered formalin. Tumor cells that penetrated the monolayer were photographed using a NIKON TiU inverted microscope with phase-contrast and fluorescence illumination. The fluorescent and phase-contrast images were overlaid using Elements BR software (Nikon, version 3.1x). A total of five non-overlapping fields was imaged per well, and the number of invaded MM1 cells (displaying a flattened morphology underneath the monolayer) was counted.

Immunoblot Analysis

To detect ligand-induced ERK1/2 activation, vector- and $LPA_2$-transfected MEF cells were serum starved 3 h before exposure to 1 µM LPA, 1 µM OTP, 10 µM GRI977143, or vehicle for 10 min. For ERK1/2 activation and PARP-1 cleavage measurements, cells were harvested in 1× Laemmli sample buffer and separated using 12% Laemmli SDS-polyacrylamide gels. To assess Bax translocation, cell lysates were separated into cytosolic, mitochondrial, and nuclear fractions using the Cell Fractionation Kit-Standard (MitoSciences; Eugene, Oreg.). Cytosolic fractions were then concentrated by precipitation with 75% trichloroacetic acid, and the pellets were dissolved in 50 mM non-neutralized Tris pH 10 buffer and 6× Laemmli buffer. Samples were boiled for 5 min and loaded onto 12% SDS-polyacrylamide gels. Western blotting was carried out as previously described (Valentine et al., 2010). Primary antibodies against pERK1/2, PARP-1, Bax (Cell Signaling Technology; Beverly, Mass.), actin (Sigma-Aldrich), and anti-rabbit-horseradish peroxidase secondary antibodies (Promega) were used according to the instructions of the manufacturer.

Detection of Ligand-Induced Macromolecular Complex Formation with $LPA_2$ $LPA_2$ forms a ternary complex with TRIP6 and NHERF2. This complex is assembled via multiple protein-protein interactions that include: binding of NHERF2 to the C-terminal PSD95/Dlg/ZO-1 domain (PDZ)-binding motif of $LPA_2$, the binding of TRIP6 to the Zinc-finger-like CxxC motif of $LPA_2$, and binding of NHERF2 to the PDZ-binding motif of TRIP6. To examine ligand-induced macromolecular complex formation, HEK293T cells were transfected with FLAG-$LPA_2$ and enhanced green fluorescent protein (EGFP)-NHERF2, and the cells were exposed to 10 µM GRI977143 for 10 min as described in detail in our previous publication (E et al., The LPA2 receptor-mediated supramolecular complex formation regulates its antiapoptotic effect. *J Biol Chem* (2009) 284: 14558-14571). The complex was pulled down using anti-FLAG M2 monoclonal antibody-conjugated agarose beads (Sigma-Aldrich) and processed for western blotting using anti-EGFP (gift from Dr. A. P. Naren; UTHSC, TN), anti-FLAG (Sigma-Aldrich), and anti-TRIP6 (Bethyl Laboratories; Montgomery, Tex.) antibodies.

Statistical Analysis

Data are expressed as mean±SD or SEM for samples run in triplicates. Each experiment was repeated at least two times. Student's t-test was used for comparison between the control and treatment groups. A p value≤0.05 was considered significant.

Figure 3:
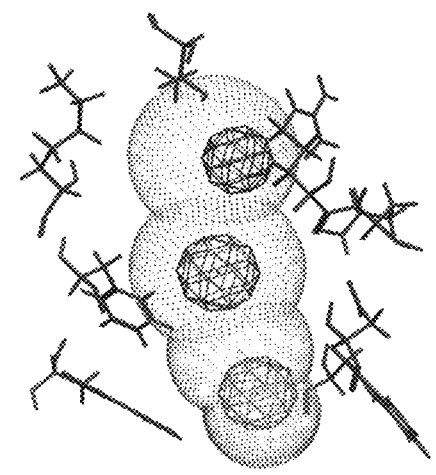
FIG. 3 is an illustration of pharmacophore development for the $LPA_2$ GPCR. The three-dimensional pharmacophore generated (panel A) was based on the common structural features of docked LPA (panel B), GRI977143 (panel C), and NSC12404 (panel D). The three agonists (ball and stick) used for pharmacophore development are shown with interactions with key amino acid residues (purple) within 4.5 Å of the previously validated ligand binding pocket.
Figure 3:
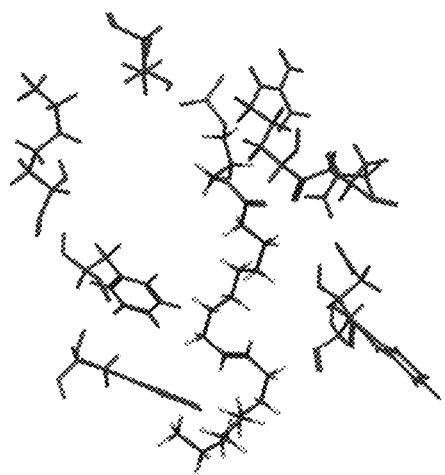
Figure 3:
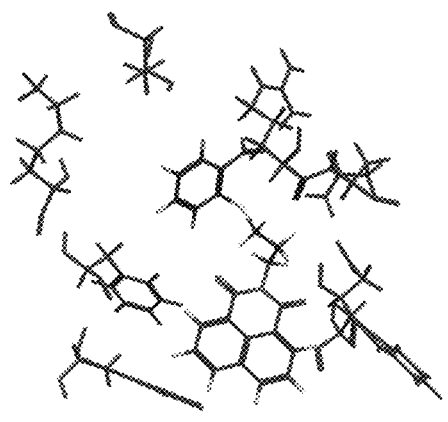
Figure 3:
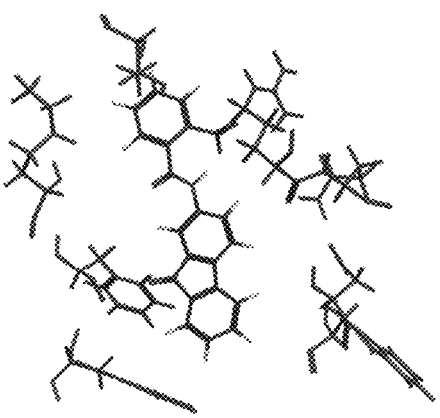

The LPA$_2$ computational model docked with LPA 18:1 suggests 13 residues that comprise the ligand binding pocket. Computational docking of the four hits indicates that these LPA$_2$ ligands interact with some additional residues unique to a specific agonist in addition to the 13 common residues. The model of GRI977143 docked to the LPA$_2$ structure is shown in FIG. 3. The docked structure shows that GRI977143 docks in the vicinity of the key residues R3.28, Q3.29, K7.36, and W4.64, which, the inventors have previously shown are required for ligand activation of LPA$_2$. In addition, the model predicted an interaction with W5.40 that was unique to this ligand.

A structure-based pharmacophore was developed using the docking function of the MOE software (Molecular Operating Environment, MOE software (2002), Chemical Computing Group, Montreal). Compound NSC12404 and LPA were docked into a homology model of LPA$_2$. In the pharmacophore model, the inventors identified three feature sites based on the interactions between the agonists and the protein. The inventors defined the key residues as those within 4.5 Å of our LPA$_2$ agonists. The pharmacophore features and the corresponding amino acid residues involved in ligand interactions are shown in FIG. 3A. This pharmacophore model has three features: a hydrophobic feature (green), a hydrogen bond acceptor (blue), and an anionic (red) feature. The four volume spheres in the pharmacophore with radii in the 2.8-4.2 Å range delineate the regions ideal for different types of chemical interactions with the ligand in the binding pocket. The distances between chemical features along with the radii of the four volume spheres are shown in FIG. 3A.

Effect of GRI977143 on Cell Growth

Figure 4:
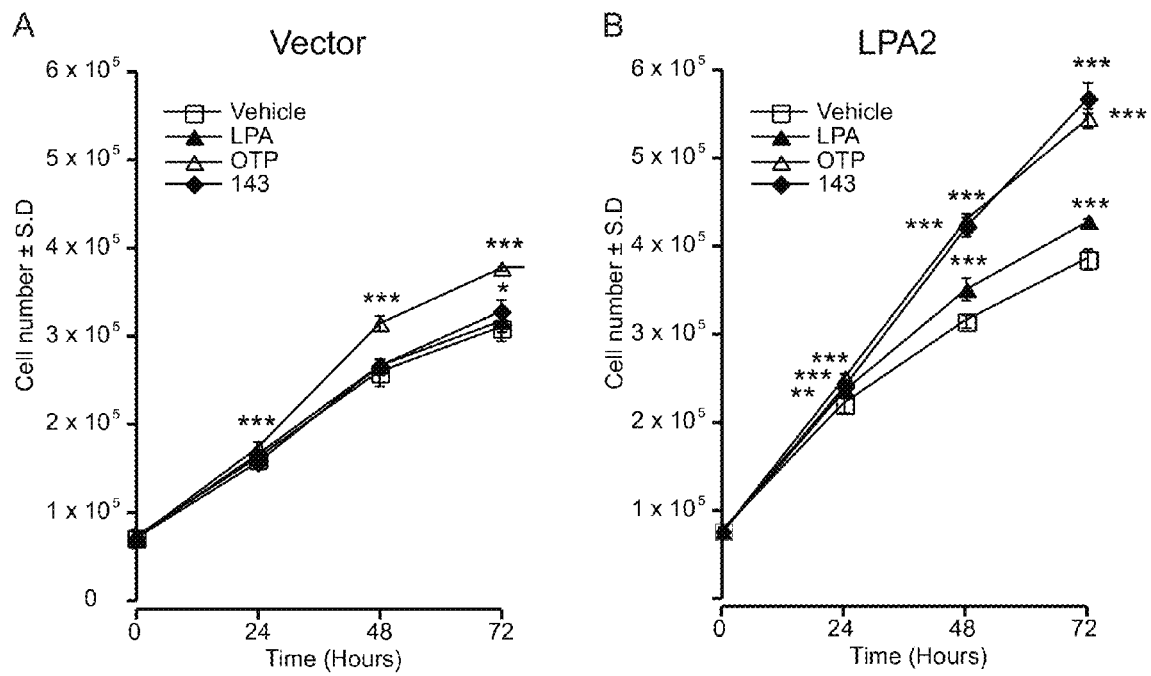
FIGS. 4A and 4B are graphs illustrating the effects of LPA (1 µM), OTP (1 µM) and GRI977143 (10 µM) on fibroblast growth. Panel A shows the growth curves of the vector- and panel B of the $LPA_2$-transduced MEF cells. Values are means±S.D and representative of two independent experiments ($*p \leq 0.05$, $p \leq 0.01$, $*p \leq 0.001$).

LPA can function as a mitogen or an anti-mitogen, depending on the cell type and the receptors it expresses. The inventors tested GRI977143 for its effect on cell proliferation of vector- (FIG. 4A) and LPA$_2$-transduced MEF cells (FIG. 4B). LPA had no significant effect on the proliferation of empty vector-transduced MEF cells. Likewise, GRI977143 did not cause a significant increase in vector cell proliferation except at 72 hours (p<0.05). In contrast, OTP significantly (p<0.001) increased the growth of empty vector transduced MEF cells from 24 hours onwards. The effects of LPA, OTP and GRI977143 on the growth of LPA2-transduced MEF were all significant from 24 hours onwards.

Effect of GRI977143 on MM1 Hepatoma Cell Invasion

Figure 5:
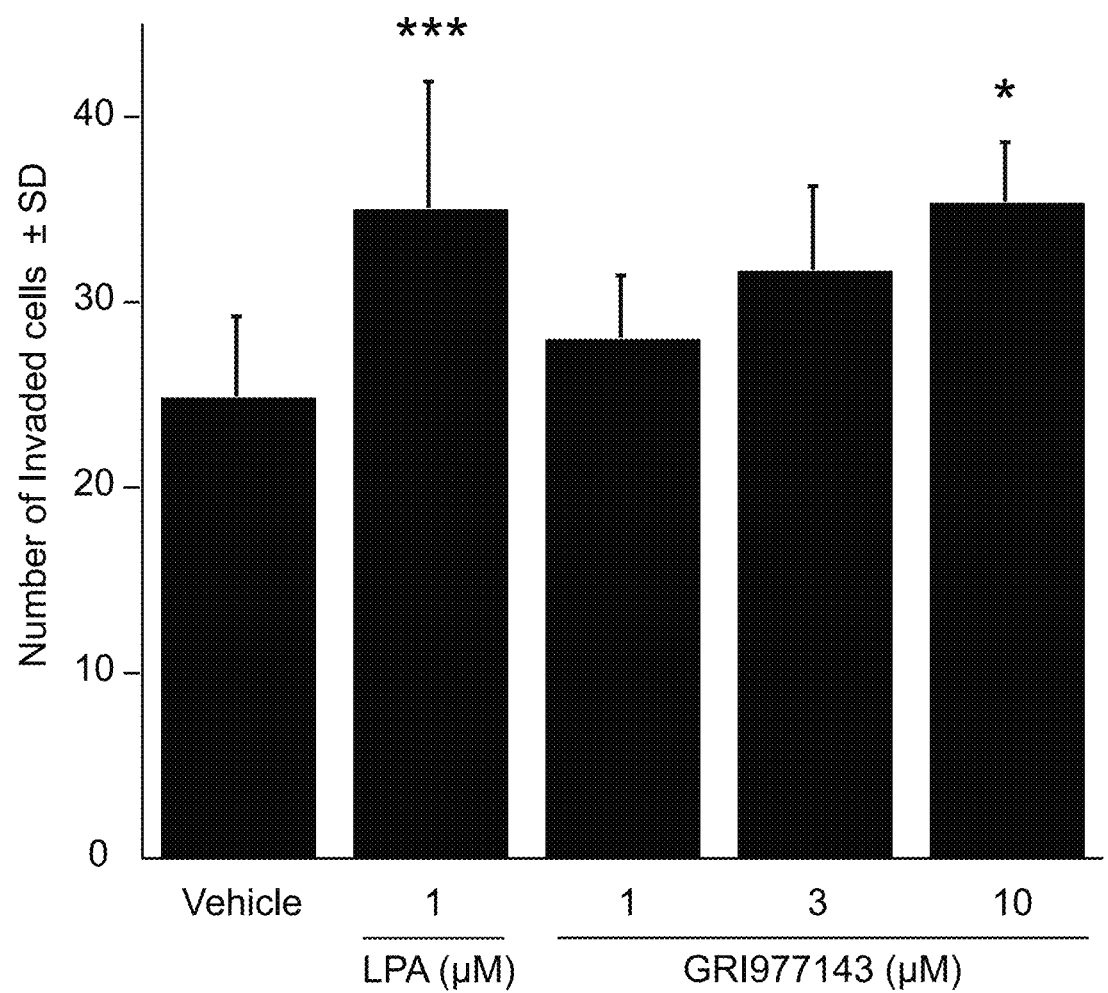
FIG. 5 is a bar graph illustrating the effect of GRI977143 on the invasion of HUVEC monolayers by MM1 hepatocarcinoma cells. Data are the means of 5 non-overlapping fields and representative of two independent experiments ($*p \leq 0.05$, $***p \leq 0.001$).

The highly invasive rat hepatoma MM1 cells invade mesothelial cell monolayers in an LPA-dependent manner. The LPA$_2$ receptor is abundantly expressed in MM1 cells. The inventors questioned whether GRI977143-mediated activation of LPA$_2$ could stimulate the invasion of HUVEC monolayers by MM1 cells, and their results showed that whereas 1 μM LPA caused a significant increase in MM1 cell invasion, a higher (10 μM) concentration of GI977143 was required to elicit the same significant increase in invasion (FIG. 5).

Figure 6:
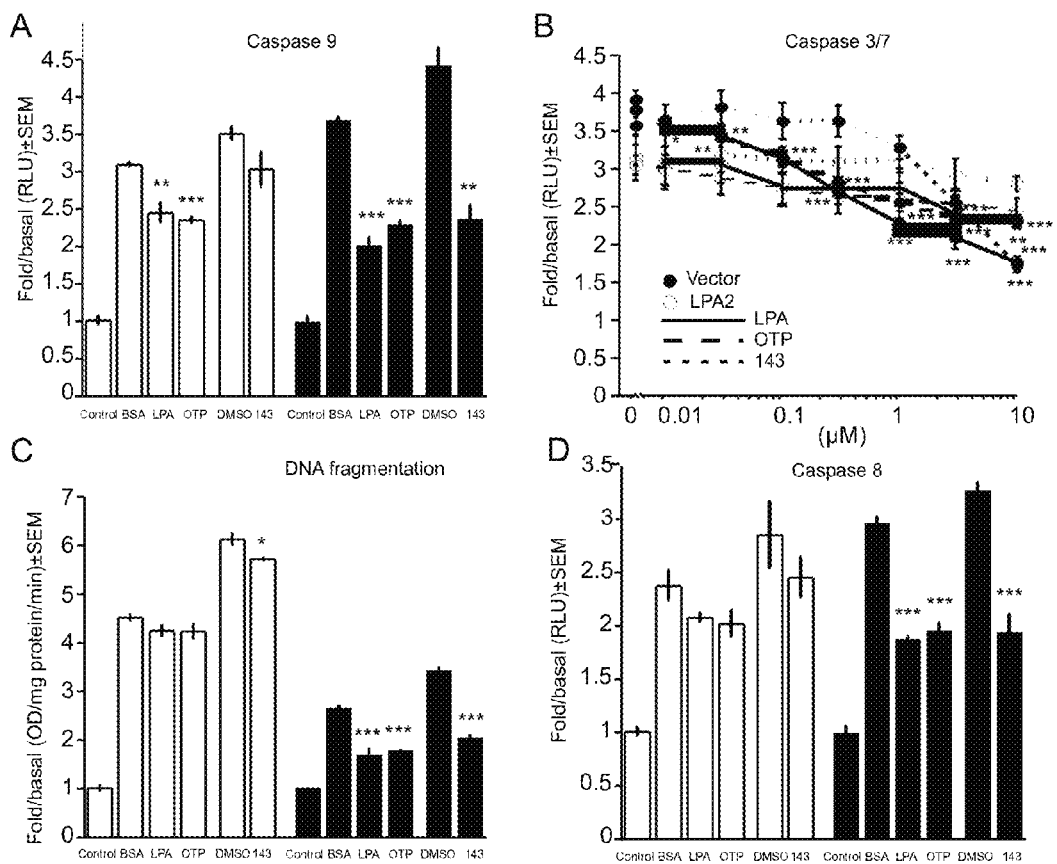
FIG. 6 is a series of bar graphs illustrating the effects of LPA (panels A, B, D: 1 µM; panel C: 3 µM), OTP (panels A, B, D: 1 µM; panel C: 3 µM), and GRI977143 (10 µM) on Adriamycin-induced apoptotic signaling in vector- (open bars) or $LPA_2$-transduced (filled bars) MEF cells. Bars and data points represent the mean of triplicate wells and the data are representative of three independent experiments. ($*p \leq 0.05$, $p \leq 0.01$, $*p \leq 0.001$).

Effect of GRI977143 on LPA$_2$-Mediated Protection Against Adriamycin-Induced Apoptosis The inventors examined the antiapoptotic properties of GRI977143 using Adriamycin to induce apoptosis. GRI977143 (10 μM) decreased caspase 9 activation in LPA$_2$-transduced MEF cells by 46±4%, this decrease being similar in its magnitude to that of 1 μM LPA, whereas 1 μM OTP resulted in a slightly smaller 38±1% decrease (FIG. 6A). GRI977143 did not affect caspase 9 activation in the vector-transduced cells, whereas LPA and OTP even in a 1-μM concentration reduced caspase 9 activation by 20-24% (FIG. 6A). The inventors next tested the effect of their test compounds on Adriamycin-induced caspase 3 and 7 activation in vector- and LPA$_2$ transduced MEF cells. GRI977143 elicited a significant protection (p<0.01) above 3 μM. At 10 μM concentration, GRI977143 reduced caspase 3 and 7 activation to a similar degree as 10 μM LPA, but surpassed the effect of 10 μM OTP. LPA and OTP protected LPA$_2$-transduced MEF cells. However, at 10 μM, LPA also had an inhibitory effect in the vector-transduced cells by 26±1%. In contrast, when applied at 10 μM, GRI977143 and OTP did not attenuate caspase 3/7 in the vector-transduced cells (FIG. 6B).

To further characterize the effect of GRI977143 on apoptosis, the inventors measured Adriamycin-induced DNA fragmentation in vector- and LPA$_2$ MEF cells. In LPA$_2$-transduced MEF cells GRI977143 reduced DNA fragmentation by 41±2% (p<0.001) compared to a modest 7±1% protection in the vector-transduced cells (p<0.05). 3 μM LPA and 3 μM OTP also protected LPA$_2$-transduced MEF cells by decreasing DNA fragmentation by 35±4% and 32±1%, respectively (FIG. 6C). They also examined the effect of GRI977143 on caspase-8 activation in the Adriamycin-induced apoptosis model. Administration of 10 μM GRI977143 resulted in a 41±5% decrease in caspase-8 activation in LPA$_2$- transduced MEF cells. Treatments with 1 μM LPA or 1 μM OTP decreased caspase 8 activation by 36±1% and 33±2%, respectively. A similar but lesser effect of LPA and OTP was noted in the vector-transduced cells, amounting to 12±2% and 15±5% decreases, respectively (FIG. 6D). These findings together establish that selective activation of LPA$_2$ receptor signaling by GRI977143 protects against Adriamycin-induced apoptosis by inhibiting caspase 3, 7, 8 and 9, and reducing DNA fragmentation.

GRI977143 Reduces Apoptosis Induced by Serum Withdrawal in MEF Cells

Figure 7:
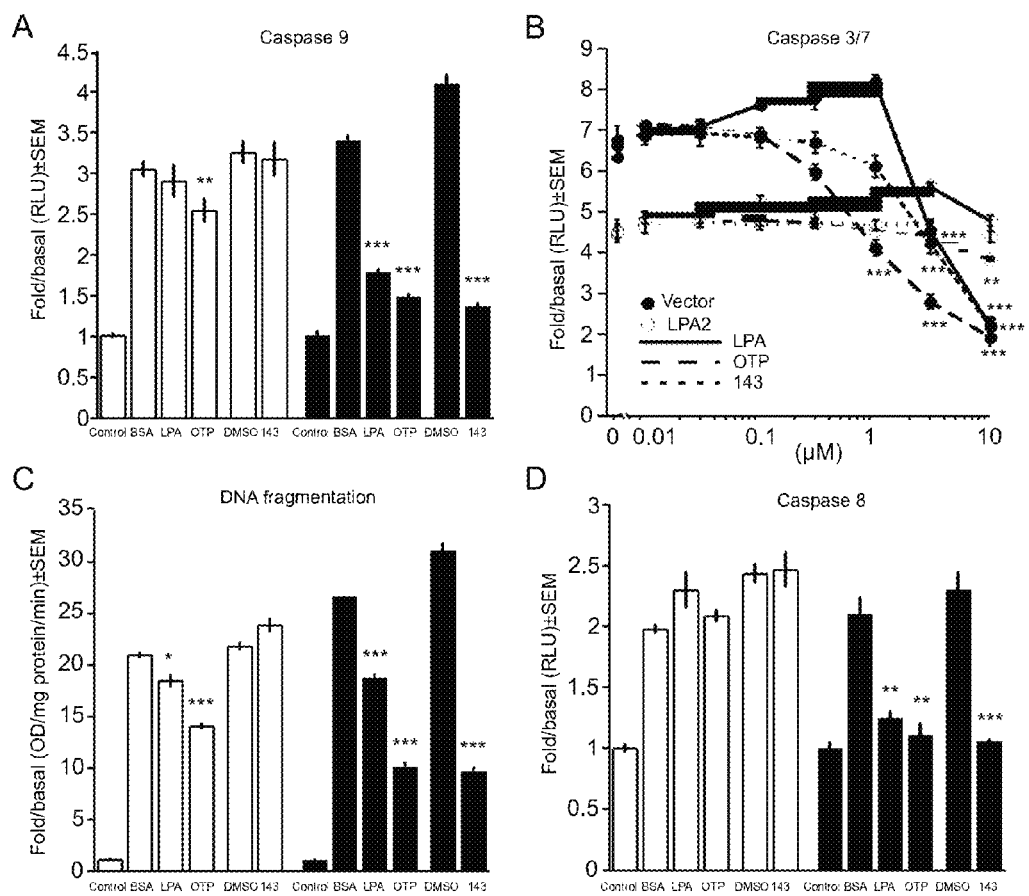
FIG. 7 is a series of bar graphs illustrating the effects of LPA (panel A & B: 3 µM; panels C, D: 10 µM), OTP (3 µM), and GRI977143 (10 µM) on serum withdrawal-induced apoptotic signaling in vector- (open bars) or $LPA_2$-transduced (filled bars) MEF cells. Bars and data points represent the mean of triplicate wells and the data are representative of three independent experiments. ($*p \leq 0.05$, $p \leq 0.01$, $*p \leq 0.001$).

The inventors also examined whether GRI977143 could provide the necessary trophic support to serum starved MEF cells expressing or lacking LPA$_2$ receptors. Experiments with this paradigm showed that 10 μM GRI977143 was highly effective in reducing caspase 3, 7, 8, and 9 activation and also attenuated DNA fragmentation (FIG. 7). GRI977143 failed to cause any reduction in these apoptotic indicators in vector-transduced MEF cells. In contrast, LPA and OTP protected the vector-transduced MEF cells too. These results mirrored our findings in the Adriamycin-induced apoptosis paradigm, extending the role of LPA$_2$ activation to the prevention of serum withdrawal-induced apoptosis.

GRI977143 Inhibits TNFα-Induced Apoptosis in IEC-6 Intestinal Epithelial Cells

Figure 8:
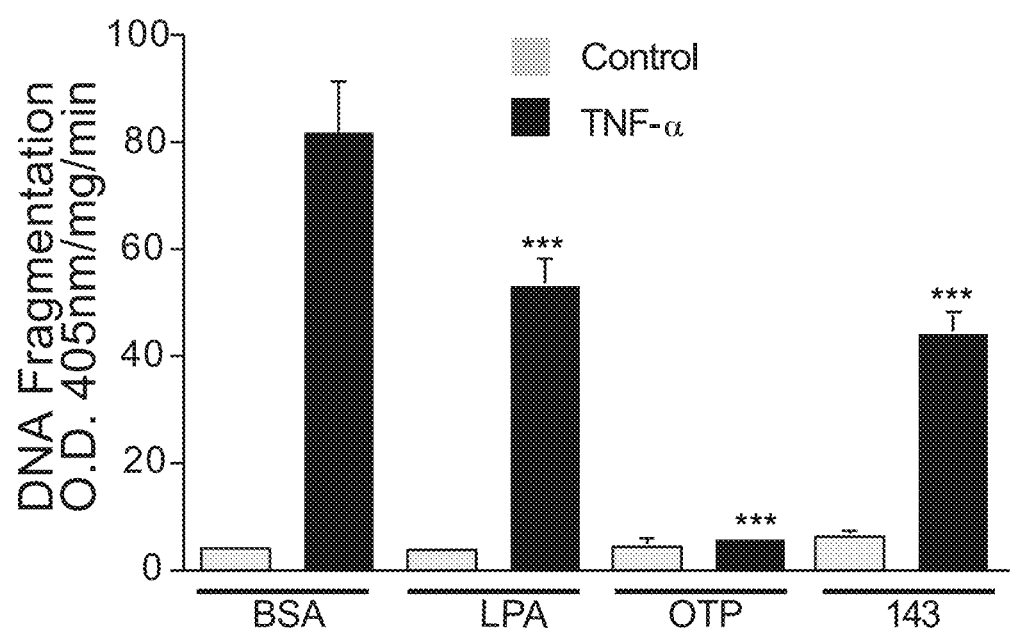
FIG. 8 is a bar graph illustrating the effects of LPA (1 µM), OTP (10 µM), and GRI977143 (10 µM) on DNA-fragmentation elicited via extrinsic apoptosis induced by TNFα and CHX treatment in IEC-6 cells. Bars represent the mean of triplicate wells, and the data are representative of two experiments. ($***p \leq 0.01$).

The inventors earlier demonstrated that LPA and OTP protects and rescues non-transformed IEC-6 crypt-like intestinal epithelial cells from TNFα-induced apoptosis. IEC-6 cells endogenously express LPA$_{1/2/3/4}$ GPCRs, GPR87 and P2Y5. Thus, the inventors tested the effect of GRI977143 in this model of extrinsic apoptosis. Treatment with TNF-α/CHX increased DNA fragmentation over 20-fold; the fragmentation was completely blocked by 10 μM OTP and significantly reduced by 1 μM LPA or 10 μM GRI977143 treatment (FIG. 8). Neither LPAR agonist caused any detectable change in DNA fragmentation when added to the cultures in the absence of TNF-α/CHX.

Figure 9:
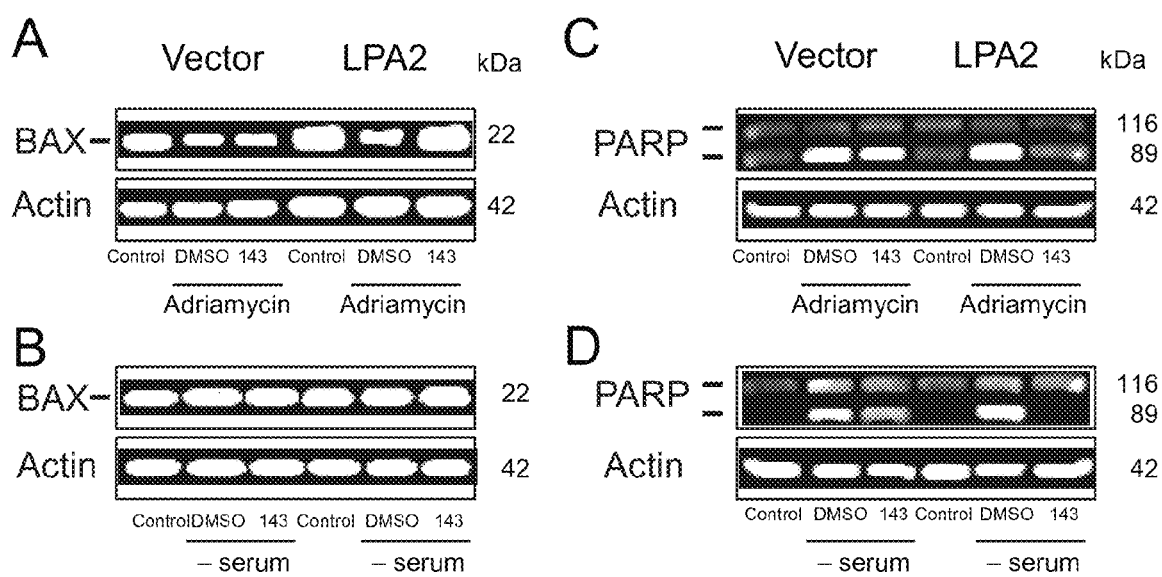
FIGS. 9A through 9D are photographs of Western blots illustrating the effects of GRI977143 on cytoplasmic Bax levels and PARP-1 cleavage in vector- or $LPA_2$-transduced MEF cells following Adriamycin- or serum withdrawal-induced apoptosis. The western blots shown are representative of three experiments.
Figure 10:
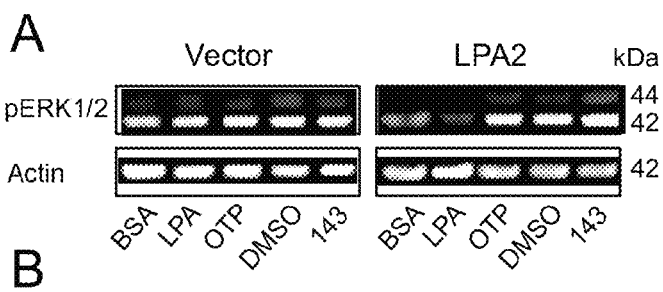
FIGS. 10A through 10C illustrate signaling pathways activated by LPA (1 µM), OTP (1 µM), or GRI977143 (10 µM). Representative western blots (panel A) and densitometry (panel B) of the mean ERK1/2 activation in vector- (open bars) and $LPA_2$-transduced (filled bars) MEF cells after GRI977143 treatment. Data were normalized for equal loading based on actin and are representative of three independent experiments ($*p \leq 0.05$, $***p \leq 0.001$). Panel C shows that GRI977143 elicits macromolecular complex assembly between FLAG-$LPA_2$, EGFP-NHERF2, and endogenous TRIP6. The blot shown is representative of two co-transfection experiments.
Figure 10:
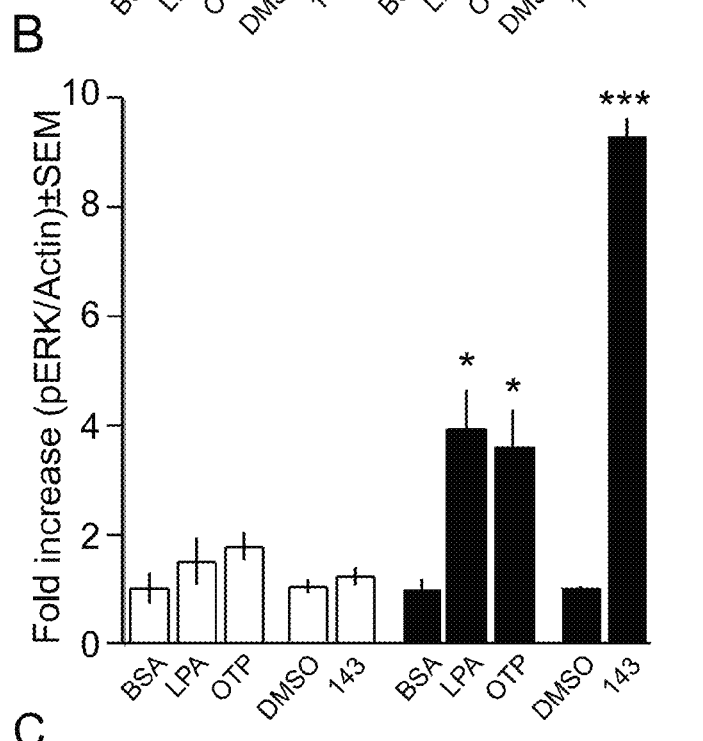
Figure 10:
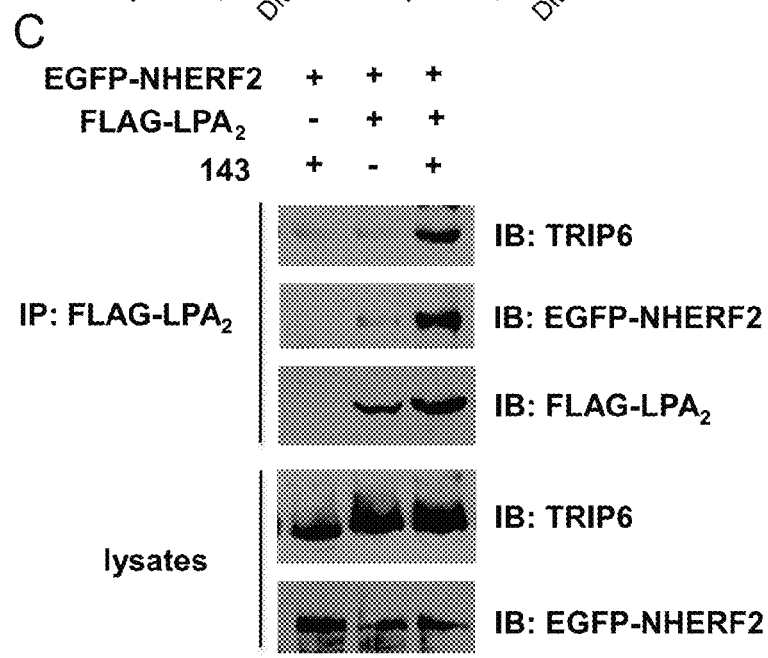
Figure 11:
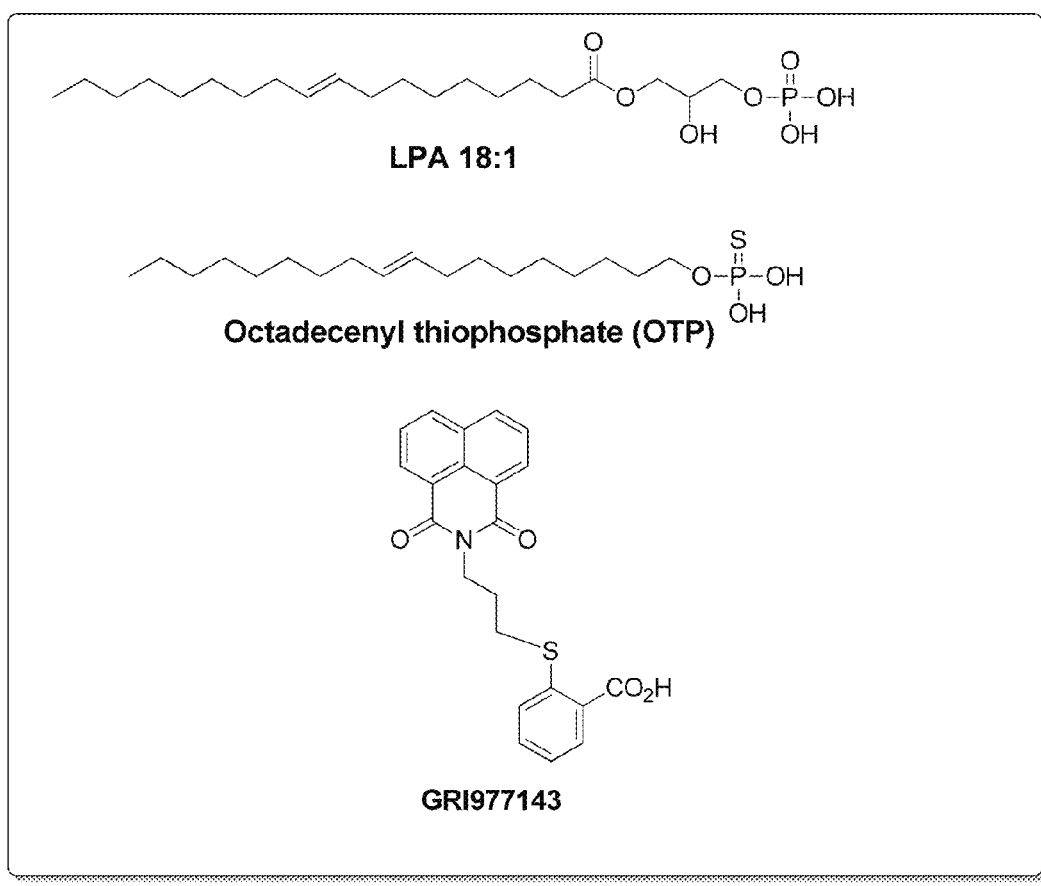
FIG. 11 illustrates the chemical structures of LPA 18:1, Octadecenyl thiophosphate (OTP), and GRI977143.
Figure 12:
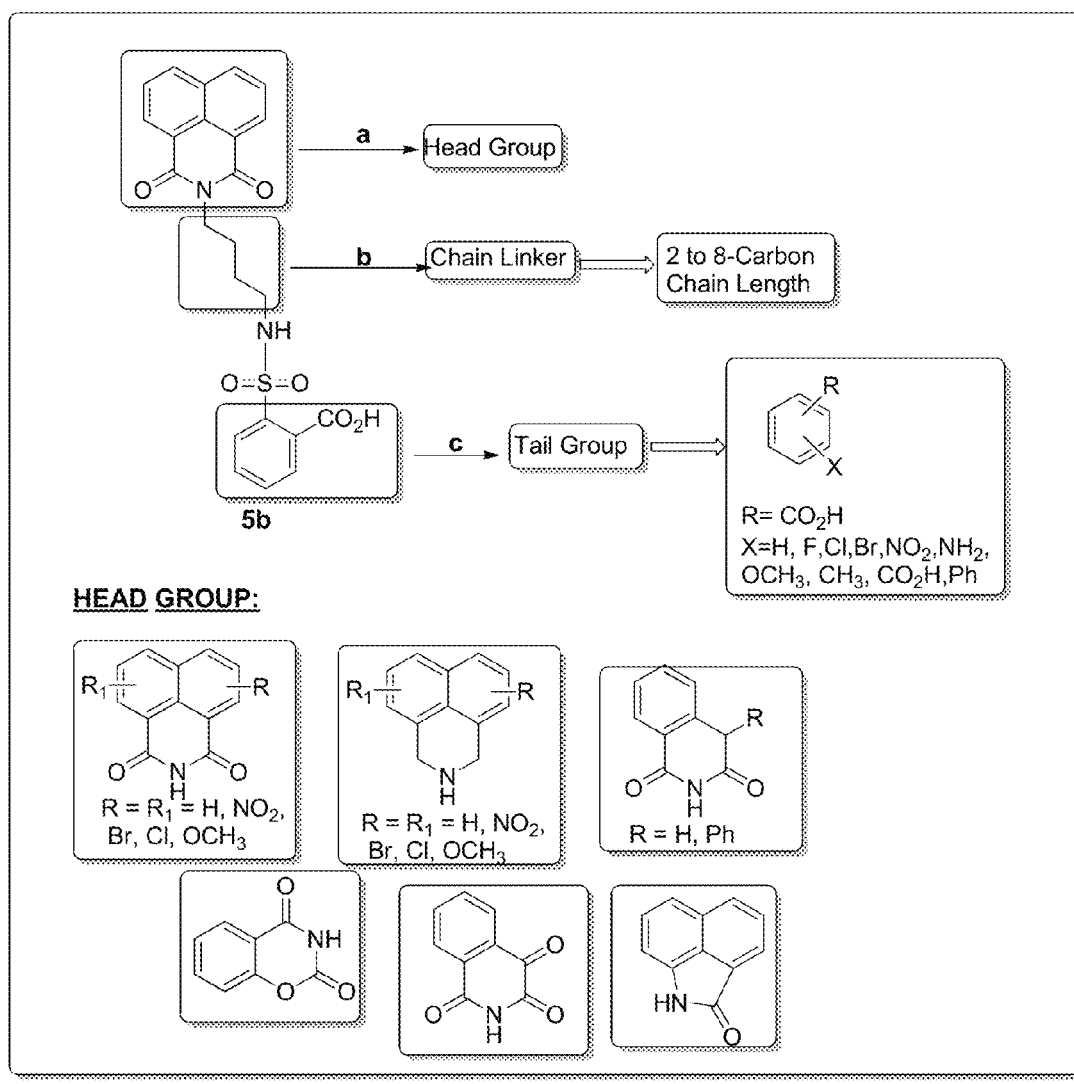
FIG. 12 illustrates structural modifications proposed by the inventors for the development of a highly-effective and specific LPA$_2$ agonist.

Effect of GRI977143 on Bax Translocation and PARP-1 Cleavage Induced by Adriamycin or Serum Withdrawal Because GRI977143 reduced activation of caspases 3, 7, 8, and 9, the inventors tested the effect of 10 μM GRI977143 on Bax translocation to the mitochondria induced by Adriamycin or serum withdrawal. As shown in FIG. 9A, 10 μM GRI977143 treatment maintained a high level of Bax in the cytoplasm of LPA$_2$-transduced MEF cells after Adriamycin treatment, consequently reducing its translocation to the mitochondria. GRI977143 failed to reduce Bax translocation in the vector-transduced MEFs. In the serum withdrawal model of apoptosis the inventors did not detect any change in cytosolic Bax level (FIG. 9B).

GRI977143 treatment (10 μM) also reduced PARP-1 cleavage after both apoptosis-inducing treatments (FIG.

9C-D). This effect was not observed in the vector-transduced cells. These experiments are consistent with the hypothesis that GRI977143 attenuates the activation of the mitochondrial apoptosis pathway through a mechanism that requires the $LPA_2$ receptor.

Effect of GRI977143 on ERK1/2 Activation

To elucidate some of the molecular mechanisms responsible for the antiapoptotic effect of GRI977143, the inventors investigated its effect on the activation of ERK1/2 kinases, which is a required step in $LPA_2$ receptor-mediated antiapoptotic signaling. Treatment with 10 µM GRI977143 for 10 min increased ERK1/2 activation 9.6-fold in $LPA_2$-transduced MEF cells but did not alter the basal activity of these kinases in the vector-transduced cells (FIG. 10A-B).

Effect of GRI977143 on the Assembly of a Macromolecular Complex Between $LPA_2$ TRIP6 and NHERF2

$LPA_2$ receptor-mediated supra-molecular complex formation is required for protection against Adriamycin-induced apoptosis. To further elucidate molecular mechanisms activated by GRI977143, the inventors investigated its effect on agonist-induced signalosome assembly between TRIP6, NHERF2 and the C-terminus of $LPA_2$. This macomolecular complex plays an important role in the antiapoptotic effect via stimulation of the ERK1/2 and protein kinase B-nuclear factor κB (Akt-NFκB) survival pathways. GRI97143 elicited the assembly of the macromolecular complex indicated by the recruitment of TRIP6 and EGFP-NHERF2 to the $LPA_2$ receptor (FIG. 10C). Only trace amounts of the ternary complex were detected in the vehicle-treated cell lysates, indicating that activation of $LPA_2$ by GRI977143 elicited the assembly of the signaling complex.

LPA has been shown to promote cancer cell invasion and metastasis. The inventors tested the effect of GRI977143 in an in vitro invasion model that has been considered a realistic model of metastasis. Lysophosphatidic acid (LPA) 18:1 purchased from Avanti Polar lipids (Alabaster, Ala.). Stock solutions of LPA were prepared in phosphate-buffered saline (PBS) with an equimolar complex of charcoal-stripped, fatty acid-free bovine serum albumin (BSA; Sigma-Aldrich, St Louis, Mo.); Compound 5b, meta-methoxy analog of GRI977143 and Compound 7b, Br-analog of GRI977143 were prepared in dimethyl sulfoxide (DMSO).

Cell Culture

Mouse embryonic fibroblast (MEF) cells used in this study isolated from LPA1/2 double knock out (LPA2-DKO) mice {Lin, 2007 #132}. These MEF express LPA4/5/6 receptors endogenously at lower levels but completely lack LPA1/2/3 receptor subtypes. The human LPA2 receptor was reintroduced into these MEF cells by lentiviral transduction, which are designated LPA2 DKO MEF {Lin, 2007 #132}. Empty vector-transduced MEF cells, designates as EV DKO MEF, were used as a control. Cells were cultured in a DMEM supplemented with 10% v/v fetal bovine serum (FBS), 2 mM L-glutamine, 100 U/ml penicillin, and 100 µg/mL streptomycin. During serum starvation, the growth medium was replaced with DMEM containing 0.1% (w/v) BSA.

Induction of Apoptosis by Adriamycin

The cells were plated in 48 well plates ($2\times10^4$ cells/well) and cultured overnight in full growth medium. Next morning the growth medium was replaced by serum-free starvation medium and cells were pretreated for 1 hour with LPA (1 or 3 µM), compound 5b or 7b (1, 3 or 10 µM). Apoptosis was elicited by 1.7 µM Adriamycin in vector and $LPA_2$ transduced MEF cells. Caspase 3, 7, 8, 9 activity and DNA fragmentation were measured to assess apoptosis 5 h after Adriamycin exposure.

Induction of Apoptosis by Direct γ-Irradiation

MEF cells were plated the day before the irradiation in 48 well plates at a density of $2\times10^4$ cell/well. One hour before the irradiation the growth medium was changed to serum-free starvation medium and the cell cultures were exposed to a dose of 15 Gy γ-irradiation, at a dose rate of 3.2 Gy/min. One hour post irradiation cells were treated with either vehicle (BSA or DMSO), LPA (1-3 µM), compound 5b, or compound 7b both at 1, 3 or 10 µM Caspase activation, DNA fragmentation were measured 4 h after the irradiation.

Caspase Activation Assay

To measure caspase activation the cells were lysed in 50 µl Caspase-Glow® reagent (Caspase 3/7, 8, 9 Promega, Madison, Wis.). The cells were shaken with the caspase reagent for 30 min at room temperature (RT). After 30 min, the luminescence was measured using a BioTek (Winooski, Vt.) plate reader. The mean caspase activity in triplicates/experimental group±SD was calculated. LPA was used as a positive control in all experiments.

DNA Fragmentation ELISA

DNA fragmentation was quantified by using the Cell Death Detection ELISA assay kit (Roche Diagnostics, Penzberg, Germany). 20 µl cell lysate was incubated with the anti-histone-biotin anti-DNA-peroxidase-conjugated antibody in a 96-well streptavidin-coated plate with shaking at RT for 2 h. After washing the wells three-times with the incubation buffer, 100 µl/well 2,2'-azino-di(3-ethylbenzthiazolin-sulfonate) substrate was added and the absorbance was measured at 405 nm. Protein concentration was measured using BCA Protein Assay Kit (Thermo Fisher Scientific Inc., Rockford, Ill.). DNA fragmentation was expressed as absorbance units/mg protein. LPA was used as a positive control in all experiments.

Effect of GRI Analogs on Radiation-Induced Mortality in C57BL/6 Mice Exposed to 15.68 Gy Partial Body Irradiation with 5% Bone Marrow Shielding (PBI-BM5)

Figure 20:
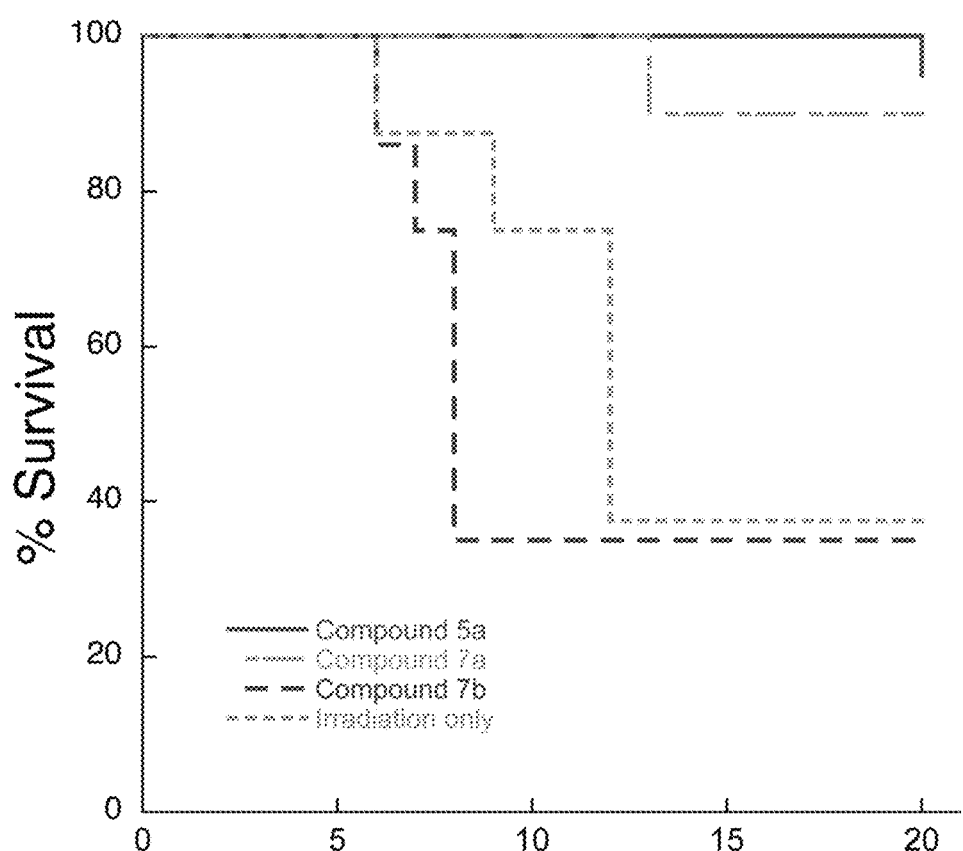
FIG. 20 is a mortality profile of C57BL/6 mice exposed to 15.68 Gy PBI-BM5 γ-irradiation. Notably, compounds 5a and 7a significantly reduced mortality (p<0.001), whereas compound 7b in this dosing and formulation was ineffective. The group sizes were 16-20 mice/group.
Figure 21:
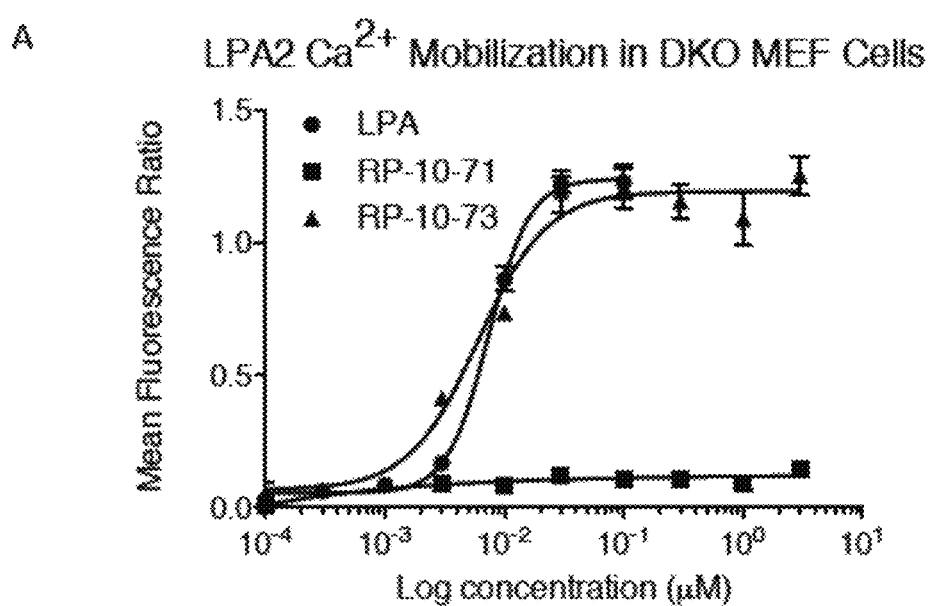
FIG. 21 is a graph illustrating the results of Fura-2AM Ca2+ Assay for Agonism of compounds RP-10-71 and RP-10-73. To determine the EC50 values of RP-10-71 and RP-10-73 compared to LPA18:1 in Ca2+ mobilization, triplicate wells of Fura-2AM-loaded LPA$_2$ DKO MEF cells were treated with 0.0003-0.1 µM LPA18:1 or 0.003-3 µM RP compounds in the presence of equimolar BSA in Krebs buffer. Fluorescence was read every 3.42 seconds for a total of 70 seconds at Ex/Emλ of 340/510 nm and 380/510 nm. Data (relative fluorescence) was then recorded as a mean fluorescence ratio value of the triplicates for each concentration. Graph Pad Prism version 5.0a was then used to fit a non-linear regression curve in a variable slope model (A) to determine the EC50, Emax, and curve fit ($R^2$)(B). Numerical results are shown in Table 3 in the Examples.

10-week old female C57BL/6 mice were exposed to a 15.68 Gy (~$LD_{60/8-10}$) dose of γ-irradiation from a $^{137}Cs$ Source. Twenty four hours after irradiation mice were treated with a single 200 µL subcutaneous injection of 1 mg/kg of the test compounds 5b, 7a, and 7b dissolved in 0.8% DMSO, 1% ethanol, 2% propanediol in PBS buffer. The animals were observed daily and provided with food and water ad libitum. Form day four onward the mice also were provided with a gel food diet. The study endpoint was mortality by day 20. Results are shown in FIG. 20. Notably, compounds 5a and 7a significantly reduced mortality (p<0.001), whereas compound 7b in this dosing and formulation was ineffective.

Fura-2AM Ca2+ Assay for Agonism of RP-10-71 and RP-10-73

To determine the EC50 values of RP-10-71 and RP-10-73 compared to LPA18:1 in Ca2+ mobilization, triplicate wells of Fura-2AM-loaded $LPA_2$ DKO MEF cells were treated with 0.0003-0.1 µM LPA18:1 or 0.003-3 µM RP compounds in the presence of equimolar BSA in Krebs buffer. Fluorescence was read every 3.42 seconds for a total of 70 seconds at Ex/Emλ of 340/510 nm and 380/510 nm. Data (relative fluorescence) was then recorded as a mean fluorescence ratio value of the triplicates for each concentration. Graph Pad Prism version 5.0a was then used to fit a non-linear regression curve in a variable slope model (A) to determine the EC50, Emax, and curve fit ($R^2$)(B). Results are shown in Table 3.

TABLE 3

$LPA_2$ $Ca^{2+}$ Mobilization in DKO MEF Cells: Pharmacodynamics

| | $EC_{50}$ (nM) | $E_{max}$ (MFR) | Fit ($R^2$) |
|---|---|---|---|
| LPA 18:1 | 7.4 | 1.2 | 0.99 |
| RP-10-71 | N/A | N/A | 0.67 |
| RP-10-73 | 6.0 | 1.2 | 0.96 |

What is claimed is:
1. A compound of Formula I
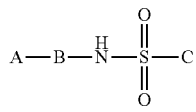 (I)
wherein A is
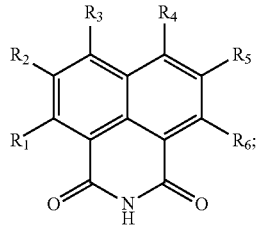
R is H or substituted or unsubstituted phenyl;
$R_1$, $R_2$, $R_3$, $R_4$, $R_5$, and $R_6$ are independently H, $NO_2$, Br, Cl, or $OCH_3$;
B is $C_2$ to $C_8$ alkyl or alkenyl; and
C is
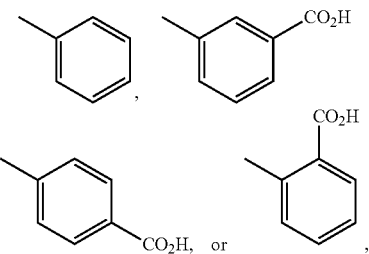
optionally substituted with F, Cl, Br, $NO_2$, $NH_2$, $OCH_3$, $CH_3$, $CO_2H$, or phenyl.
2. The compound of claim 1 wherein C is
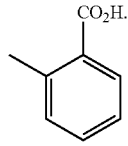
* * * * *